(12) United States Patent
Tapper et al.

(10) Patent No.: US 9,999,783 B2
(45) Date of Patent: *Jun. 19, 2018

(54) LIGHT THERAPY SPOT APPLICATOR

(71) Applicant: Johnson & Johnson Consumer Inc., Skillman, NJ (US)

(72) Inventors: Jay Tapper, Wayne, PA (US); Lawrence A. Blaustein, Chagrin Falls, OH (US); David Shuter, Palm Beach Gardens, FL (US); Charles Peter Althoff, New York, NY (US); Bradley Feild Craddock, Brooklyn, NY (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/589,004

(22) Filed: May 8, 2017

(65) Prior Publication Data

US 2017/0239490 A1    Aug. 24, 2017

Related U.S. Application Data

(60) Continuation of application No. 14/747,145, filed on Jun. 23, 2015, which is a continuation-in-part of
(Continued)

(51) Int. Cl.
*A61N 5/06* (2006.01)
*A61N 5/067* (2006.01)

(52) U.S. Cl.
CPC ...... *A61N 5/0616* (2013.01); *A61N 2005/067* (2013.01); *A61N 2005/0626* (2013.01);
(Continued)

(58) Field of Classification Search
CPC .......... A61N 5/06–2005/073; A61B 2090/036; A61B 2090/049; A61B 2017/00057;
(Continued)

(56) References Cited

U.S. PATENT DOCUMENTS

| 1,626,617 A | 5/1927 | Last |
| 1,692,669 A | 11/1928 | Last |

(Continued)

FOREIGN PATENT DOCUMENTS

| CN | 1738663 A | 2/2006 |
| DE | 20 20009 000 891 U1 | 7/2009 |

(Continued)

OTHER PUBLICATIONS

PCT/2016/038606—PCT Notification Concerning Transmittal of Int'l Preliminary Report on Patentability dated Nov. 15, 2016 (Johnson & Johnson Consumer, Inc.).

(Continued)

*Primary Examiner* — Gary Jackson
*Assistant Examiner* — Jonathan Kuo
(74) *Attorney, Agent, or Firm* — Fay Sharpe LLP

(57) ABSTRACT

Phototherapy systems comprising a therapeutic lamp platform for radiant lamps such as LEDs disposed in a holdable spot applicator assembly, the holdable spot applicator assembly including a reflective surface facing towards a patient and a plurality of LEDs for communicating lamp radiation from the lamps to a user. The lamps and associated circuitry are housed within a holdable elongated structure.

24 Claims, 24 Drawing Sheets

Related U.S. Application Data application No. 14/324,453, filed on Jul. 7, 2014, which is a division of application No. 13/604,012, filed on Sep. 5, 2012, now Pat. No. 8,771,328, said application No. 14/747,145 is a continuation-in-part of application No. 14/567,552, filed on Dec. 11, 2014, now Pat. No. 9,789,333.

(60) Provisional application No. 61/532,140, filed on Sep. 8, 2011, provisional application No. 61/914,624, filed on Dec. 11, 2013.

(52) U.S. Cl.
CPC ............... *A61N 2005/0644* (2013.01); *A61N 2005/0647* (2013.01); *A61N 2005/0652* (2013.01); *A61N 2005/0654* (2013.01); *A61N 2005/0659* (2013.01); *A61N 2005/0663* (2013.01); *A61N 2005/0666* (2013.01)

(58) Field of Classification Search
CPC .......... A61B 2018/00624; A61B 18/20–28/28; A61H 2201/02–2201/107
USPC .................................... 607/88–91; 606/9–19
See application file for complete search history.

(56) References Cited

U.S. PATENT DOCUMENTS

| | | | |
|---|---|---|---|
| 3,279,468 A | 10/1966 | Le Vine | |
| 3,376,870 A | 4/1968 | Yamamoto et al. | |
| 3,971,387 A | 7/1976 | Mantell | |
| 5,085,227 A | 2/1992 | Ramon | |
| 5,616,140 A | 4/1997 | Prescott | |
| 5,824,023 A | 10/1998 | Anderson | |
| 5,913,883 A | 6/1999 | Alexander et al. | |
| 6,045,575 A | 4/2000 | Rosen et al. | |
| 6,290,713 B1 | 9/2001 | Russell | |
| 6,293,900 B1 | 9/2001 | Bove et al. | |
| 6,350,275 B1 | 2/2002 | Vreman | |
| 6,443,978 B1 | 9/2002 | Zharov | |
| 6,447,537 B1 | 9/2002 | Hartman | |
| 6,471,716 B1 | 10/2002 | Pecukonis | |
| 6,508,813 B1 | 1/2003 | Altshuler | |
| 6,511,475 B1 | 1/2003 | Altshuler et al. | |
| 6,517,532 B1 | 2/2003 | Altshuler et al. | |
| 6,743,249 B1 | 6/2004 | Alden | |
| 6,824,265 B1 | 11/2004 | Harper | |
| 6,860,896 B2 | 3/2005 | Leber et al. | |
| 7,084,389 B2 | 8/2006 | Spector | |
| 7,125,416 B2 | 10/2006 | Kent et al. | |
| 7,198,633 B1 | 4/2007 | Starwynn | |
| 7,222,995 B1 | 5/2007 | Bayat et al. | |
| 7,290,896 B2 | 11/2007 | Dallas et al. | |
| 7,438,409 B2 | 10/2008 | Jordan | |
| 7,517,107 B2 | 4/2009 | Dallas et al. | |
| 7,520,630 B2 | 4/2009 | Murphy | |
| 7,824,241 B2 | 11/2010 | Duprey | |
| 7,896,908 B2 | 3/2011 | Ripper et al. | |
| 8,192,473 B2 | 6/2012 | Tucker et al. | |
| 8,252,033 B2 | 8/2012 | Tucker et al. | |
| 8,313,518 B2 | 11/2012 | Ripper et al. | |
| 8,491,118 B2 | 7/2013 | Waters | |
| 8,771,328 B2 | 7/2014 | Tapper et al. | |
| 8,858,607 B1 | 10/2014 | Jones | |
| 2003/0199800 A1 | 10/2003 | Levin | |
| 2004/0162549 A1 | 8/2004 | Altshuler | |
| 2005/0070977 A1 | 3/2005 | Molina | |
| 2005/0080465 A1 | 4/2005 | Zelickson et al. | |
| 2005/0182460 A1 | 8/2005 | Kent | |
| 2005/0278003 A1 | 12/2005 | Feldman | |
| 2006/0173514 A1 | 8/2006 | Biel et al. | |
| 2006/0217690 A1 | 9/2006 | Bastin et al. | |
| 2006/0217787 A1 | 9/2006 | Olson et al. | |
| 2006/0268220 A1 | 11/2006 | Hogan | |
| 2007/0032847 A1 | 2/2007 | Weckwerth | |
| 2007/0156208 A1 | 7/2007 | Havell et al. | |
| 2007/0208395 A1 | 9/2007 | Leclerc et al. | |
| 2007/0233208 A1 | 10/2007 | Kurtz et al. | |
| 2008/0065056 A1 | 3/2008 | Powell et al. | |
| 2008/0269849 A1 | 10/2008 | Lewis | |
| 2009/0143842 A1 | 6/2009 | Cumbie et al. | |
| 2009/0192437 A1 | 7/2009 | Soltz et al. | |
| 2010/0069898 A1 | 3/2010 | O'Neil et al. | |
| 2010/0121419 A1 | 5/2010 | Douglas | |
| 2011/0015707 A1 | 1/2011 | Tucker et al. | |
| 2011/0040355 A1 | 2/2011 | Francis | |
| 2011/0160814 A2 | 6/2011 | Tucker et al. | |
| 2011/0257467 A1 | 10/2011 | Clegg et al. | |
| 2011/0270365 A1* | 11/2011 | Hamada ............... | A61B 18/203 607/90 |
| 2012/0116485 A1 | 5/2012 | Burgmann | |
| 2012/0323064 A1 | 12/2012 | Kim | |
| 2015/0025602 A1 | 1/2015 | Cacciola et al. | |

FOREIGN PATENT DOCUMENTS

| | | |
|---|---|---|
| EP | 1 074 275 A1 | 2/2001 |
| EP | 1 916 016 A1 | 4/2008 |
| GB | 2 380 134 A | 4/2003 |
| WO | WO 2004052238 | 12/2003 |
| WO | WO 2006/028461 A2 | 3/2006 |
| WO | WO 2010/076707 A1 | 7/2010 |
| WO | WO 2011049419 | 10/2010 |

OTHER PUBLICATIONS

PCT/2016/038607—PCT Notification Concerning Transmittal of Int'l Preliminary Report on Patentability dated Sep. 29, 2016 (Johnson & Johnson Consumer, Inc.).

PCT/2016/038608—PCT Notification Concerning Transmittal of Int'l Preliminary Report on Patentability dated Sep. 29, 2016 (Johnson & Johnson Consumer, Inc.).

PCT/2016/038612—PCT Notification Concerning Transmittal of Int'l Preliminary Report on Patentability dated Sep. 29, 2016 (Johnson & Johnson Consumer, Inc.).

PCT/US2014/069789—PCT Notification Concerning Transmittal of Int'l Preliminary Report on Patentability dated Jun. 23, 2016 (Johnson & Johnson Consumer, Inc.).

PCT/IB2009/055617—International Search Report, Authorized Officer Stefan Lohmann, dated May 3, 2010.

* cited by examiner

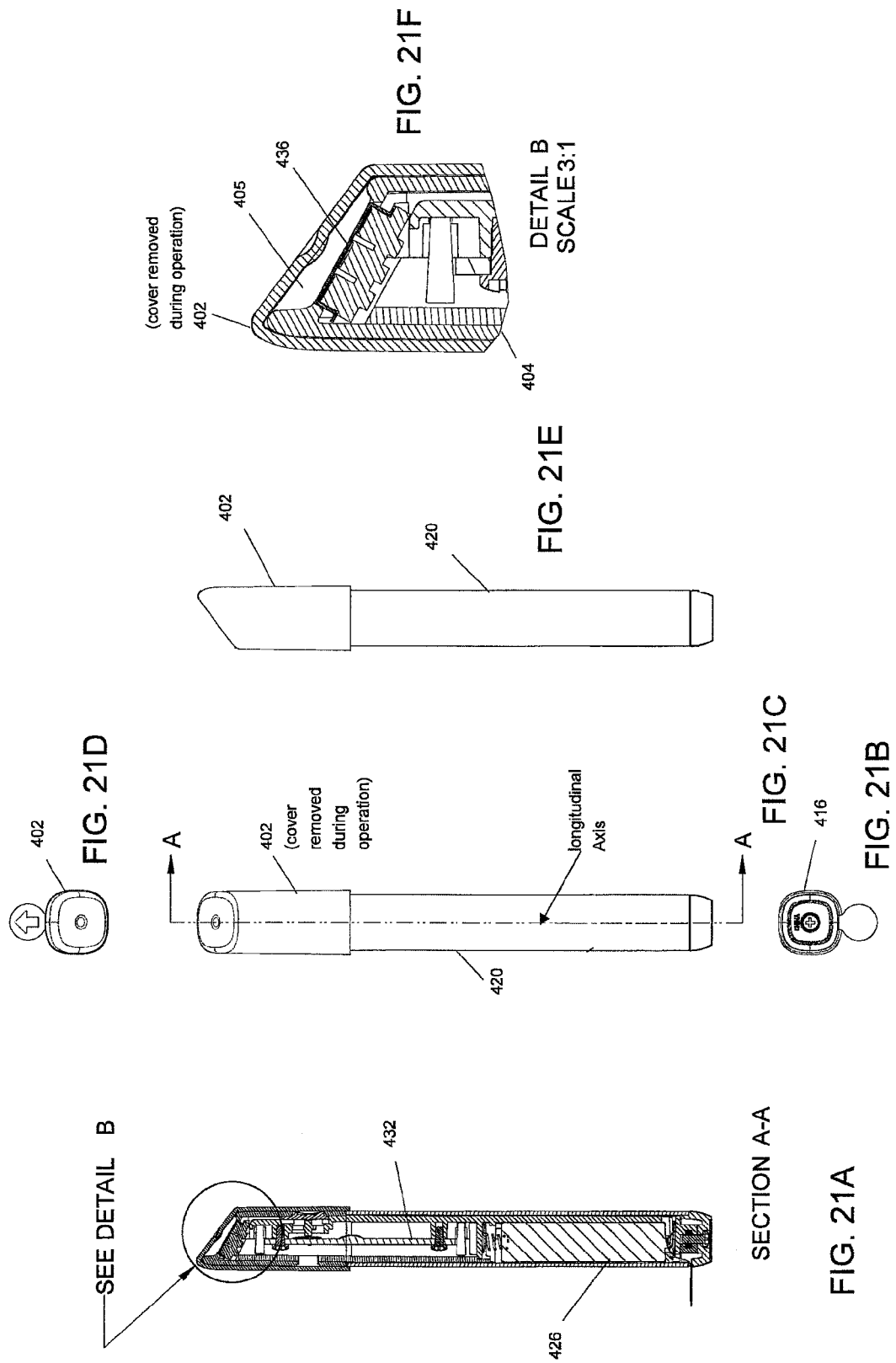

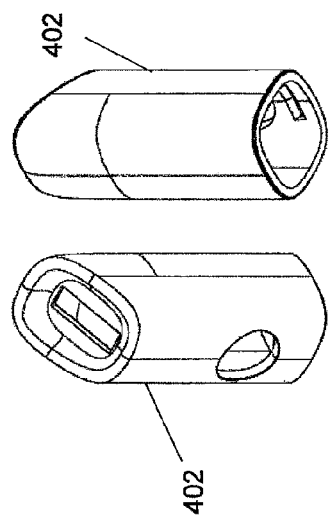
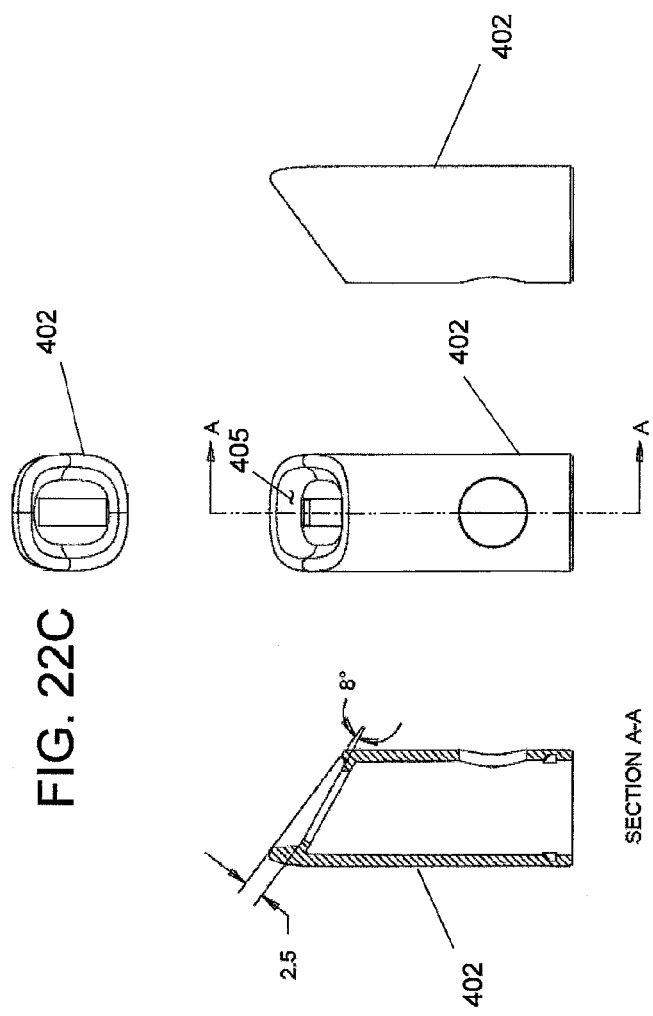
FIG. 22E
FIG. 22B
FIG. 22A
FIG. 22C
FIG. 22D

LIGHT THERAPY SPOT APPLICATOR

This application is a continuation of U.S. patent application Ser. No. 14/747,145, filed Jun. 23, 2015, which is a continuation-in-part of U.S. patent application Ser. No. 14/324,453, filed Jul. 7, 2014, which is a divisional of U.S. patent application Ser. No. 13/604,012, filed Sep. 5, 2012, now U.S. Pat. No. 8,771,328, which claims priority to U.S. Provisional Patent Application Ser. No. 61/532,140, filed Sep. 8, 2011, and which U.S. patent application Ser. No. 14/747,145, filed Jun. 23, 2015, is also a continuation-in-part of U.S. patent application Ser. No. 14/567,552, filed Dec. 11, 2014, which claims priority to U.S. Provisional Patent Application No. 61/914,624, filed Dec. 11, 2013, the disclosures of which are incorporated herein by reference.

FIELD

The present embodiments relate to devices and methods for delivering light-based skin therapy treatments for improving skin health, such as anti-aging enhancement, acne prevention, or acne treatment, using light-emitting diode (LED) light therapy, although other types of light radiating sources can be used.

BACKGROUND

Certain light spectrums emitted by LEDs (blue or red) are known to be therapeutic for skin treatment against maladies such as acne, or are beneficial to inhibit skin aging. However, there is a need to provide users/patients with a convenient at-home light therapy delivery device such as a wearable mask, veil or hood that is adjustable or flexible to conform to different sizes and shapes, and that is simple to use without user discomfort. Currently available at-home, consumer usable products on the market are fixed to one-size and/or usually have to be hand-held; which generally have not proven satisfactory for providing the best or desired light dispersion. The alternative is customers visiting a doctor's office to receive treatments.

Prior known light therapy devices, particularly masks, have suffered from problems relating to the exposure of the LEDs and the associated circuitry to power the LEDs to contact by users. More particularly, in an effort to maximize light communication to a patient, the LEDs have been disposed in a manner which allow them to be physically engaged (e.g., touched) by a patient, or even contact a treatment surface, which processes are debilitating to the LEDs as a result of the accumulation of dirt and oil. In addition, any such engagement can be dangerous to patients who are exposed to the sharp or hot edges of the LEDs and the associated circuitry. The exposure of detailed circuitry presents an intimidating and unpleasant experience when the therapy requires several minutes of time for completion and the mask is disposed relatively close to the face, often causing an uncomfortable, claustrophobic sensation over time to the patient.

A hands-free therapeutic experience is always better than having to hold the device in a particular position for extended periods of time during the therapy. Numerous assemblies have been conceived for mounting masks and helmet-like devices to varieties of straps, bands, wraps and cords, which can result in a pressing of the support and mounting assembly closely against the hair or scalp of a patient. There is always a need to minimize the extent of such attachment assemblies so that on the one hand the subject device is securely attached on the patient, but also that the attaching structure has minimal consequence to the patient's comfort during the therapy itself. Being relatively light in weight, and easily and minimally supported during therapeutic use are important to consumer acceptance.

As users come in a variety of shapes and sizes, devices should be size or area adjustable so that the therapy can be efficiently applied and/or selectively intensified to desired treatment areas.

Lastly, particularly in therapeutic devices treating facial areas, eye protection is needed to avoid light damage or irritation to a patient's eyes. Prior known devices have typically used separable patches which must rest on the eye area to block the therapeutic light from communication to the eye system itself. There is a need for a better way that is readily adaptable to communicate therapeutic light to areas near the eyes, particularly with regard to anti-aging treatments, and still protect the patient.

According to another aspect of this disclosure, embodiments of a holdable spot light therapy treatment device are disclosed. The light therapy spot application addresses the need to treat a relatively small area of a user's treatment area, such as the user's face, to prevent and/or treat a skin condition such as acne. While this disclosure initially describes a light therapy platform system including a facial mask, additional embodiments are illustrated and described to include the disclosed light therapy technology into a holdable light therapy spot applicator.

As with the light therapy facial mask platform, the light therapy spot applicator disclosed provides a convenient at-home light therapy delivery device.

It is desired to provide alternative means of using the benefits of the light therapy in a manner to maximize therapeutic efficiencies in exposure while maintaining ease and convenience of use. For this reason, a variety of light weight, flexible and adjustable embodiments are disclosed within this disclosure incorporating a variety of energy varying applications responsive to user conditions or needs.

SUMMARY

The present embodiments comprise phototherapy systems and devices comprising a therapeutic lamp platform for radiant lamps such as LEDs are disposed in an assembly comprising a first wall to which the lamps are affixed thereto and a second wall, closer to the patient, spaced from the first wall wherein the lamps are recessed relative thereto. The second wall comprises a reflective surface facing towards a patient and a plurality of light apertures substantially aligned with the LEDs on the first wall for communicating lamp radiation from the lamps to a user. The lamps and associated circuitry are disposed between the first and second wall so that the reflective surface is relatively smooth and seamless towards the patient. The number of lamps are minimized, as is the circuitry therefor, and other assembly materials are purposefully selected for a relatively light weight assembly resulting in enhanced user comfort during therapy sessions. The walls have a malleable rigidity for flexible adjustability relative to the user. More particularly, the walls have a concave configuration relative to the face of the user which is adjustable relative to a rest position to be expandable relative to a size of the head of the user for a close fitting and secure engagement to the user during use. The device is mounted to the user with a frame comprising an eyeglass frame or goggles including lenses for shielding the user's eyes from lamp radiation. The adjustability of the embodiments is further enhanced by the walls being pivotable relative to the support frame and where the frames may include telescopic temple arms for selective adjustability relative to the head size of the user. The device is thus supported on the patient as a wearable hands-free mask or the like. A power source communicates energy to the lamps and comprises a remote battery pack and may also include a control processor for counting the number of uses by the device for the user and for indicating a need for device replacement after a predetermined number of uses.

The present embodiments comprise an adjustable/flexible platform for providing a light-based therapy that is adaptable to the user's receptive surfaces, whether based on size or condition, wherein the light therapy can be applied without limitation of the kind of light and without limitation of the ultimate purpose of the therapy, i.e., beauty, health, and/or wound healing. Such sources can vary in the form of the radiant energy delivery. Pulsed light (IPL), focused light (lasers) and other methods of manipulating light energy are encompassed within the present embodiments. Other methods of light emission may comprise continuous, pulsed, focused, diffuse, multi wavelength, single wavelength, visible and/or non-visible light wavelengths.

A present embodiment describes forms such as a shaped/fitted mask, goggles, eye mask, shroud or hood, and facial mask (collectively referred to as "mask") with LED light emitted from LED bulbs or LED strips that are capable of being adjusted to accommodate the variances in face size or areas intended for therapeutic attention. Control systems are included to vary light intensity, frequency or direction.

The platform can be secured to the head by multiple means: eyeglass frames, straps, drawstring, harness, Velcro®, turn dial or snap and buttons. As the mask is secured it can be adjusted upward, for chin to forehead coverage. It can also be adjusted outward, for side-to-side coverage. In addition, once the platform has been bent/slid to cover the face area, the distance of the platform from the skin can be adjusted for achieving a desired light intensity relative to a user's skin surface. Thus, the light therapy can be maximized in up to three physical dimensions.

The subject adjustability may be implemented through "smart" processing and sensor systems for enhanced flexibility/adjustability in the form of adjustable energy output, adjustable wavelengths, priority zones, timers, and the like. The sensors of the sensor systems will enable the subject embodiments to have the ability to evaluate the skin of the face and body of a patient with sensors for color, wrinkles, age spots, acne, lesion density, and the like, and plan a smart treatment, utilizing more or less energy on the priority zones. The subject embodiments can be smart from the standpoint of skin type, age, overall severity of problems and have the ability to customize the treatment accordingly.

In yet another embodiment, the lamps are embedded in a flexible sheet of formable material and are integrally molded as strips within a material sheet.

In addition, control systems can measure or count device usage and communicate historical usage, and indicate a time for replacement.

The present disclosure thus describes a fully flexible and adjustable LED device which provides improved usability and light dispersion.

In still another embodiment of this disclosure, a phototherapy device comprising a therapeutic lamp platform including an elongated structure having a concave reflective end including a plurality of radiant lamps having a mixed combination of different wavelength radiant energy and disposed to communicate the radiant energy to a user treatment area, the concave reflective end communicating the radiation radiant energy to the user treatment area from the plurality of radiant lamps wherein the concave reflective end disperses the radiant energy over the user treatment area.

In another embodiment of this disclosure, a phototherapy device comprising a therapeutic lamp platform comprising an elongated structure including a concave reflective end including a plurality of radiant lamps having a mixed combination of different wavelength radiant energy and disposed to communicate the radiant energy to a user treatment area, the concave reflective end configured to communicate the radiation radiant energy to the user treatment area from the plurality of radiant lamps wherein the concave reflective end disperses the radiant energy over the user treatment area.

In still another embodiment of this disclosure, a phototherapy device comprising an elongated structure including a concave reflective end, a plurality of radiant lamps operatively disposed to communicate radiant energy from the concave reflective end to a user treatment area, wherein the concave reflective end disperses the radiant energy over the user treatment area.

BRIEF DESCRIPTION OF THE DRAWINGS

FIGS. 21A-21F illustrate various views of the light therapy spot applicator shown in FIG. 20A;

FIGS. 22A-22E illustrate various views of the shroud portion of the light therapy spot applicator shown in FIGS. 20A and 20B;

DETAILED DESCRIPTION

Figure 1:
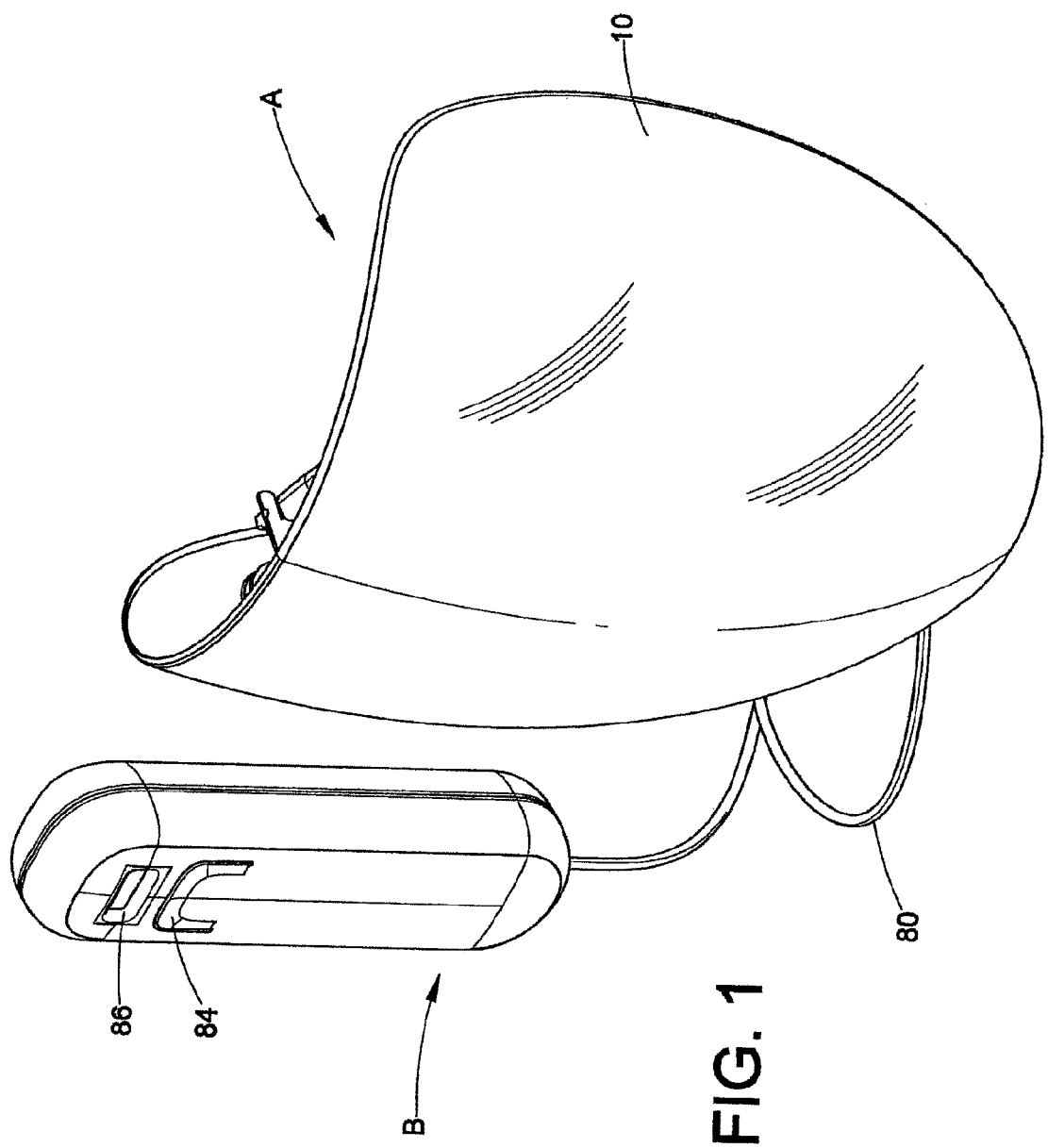
FIG. 1 is a perspective view of one embodiment of a therapeutic lamp platform comprising a wearable mask.

The subject embodiments relate to a phototherapy system including methods and devices, including a wearable hands-free device with a remote or integrated battery pack for powering therapeutic lamps in the device. The subject devices display numerous benefits including a light platform wherein the platform and the lamps therein are properly positionable relative to a user during use with no human touch according to one exemplary embodiment. That is, structural componentry of the device not only supports the lamp platform on the user, but functions as a guide for the appropriate disposition of the lamps relative to the treatment areas of the user. The structural assembly of the device precludes sharp or hot surfaces from being engageable by a user as the lamps are recessed relative to an inner reflective surface closest to and facing the patient treatment surface. Circuit componentry to communicate power to the lamps is also encased within the wall structure. Therapeutic light, shining through wall apertures, is communicated to the user while the lamps and the circuitry are effectively encased within the spaced wall structure. A smooth seamless surface is thus presented to the user that is properly spaced for the desired therapeutic treatments, yet provides improved ventilation so that an aesthetic and appealing device surface is presented to the user that minimizes user discomfort. Other benefits relate to the adjustability of the device in the form of a flexible mask which forms upon user receipt to match a treatment surface, e.g., a head size, of the user. Smart componentry not only measures device usage, but may also calculate lamp degradations so that a time for proper replacement can be communicated to a user. The overall assembly is purposefully constructed of relatively light weight and minimized componentry for ease of user use and comfort.

More particularly, and with reference to FIGS. 1-4, the subject embodiments include a lamp platform A and a remote battery pack B. The platform A is comprised of a wall structure 10 encasing the plurality of therapeutic lamps such as red and blue LEDs 12 and circuitry 14 for communicating power to the lamps via cable 80 and connector 83 from the battery pack B. Other radiant energy forms could also include fluorescents, lasers or infrareds. The wall structure 10 is mounted on a support frame 20 connected via snap-out pivotal connections 22 which allows the wall structure to adjust position via a slight pivot relative to the frame 20. The frame 20 also includes protective lenses 24 and a nose bridge 26. The temple arms 28 may be fixed or telescopic and hinge relative to the frame 20 so that the platform A can be mounted on a user in a hands-free support manner via resting on the nose with the nose bridge 26 and the ears with temple arms 28.

Figure 3:
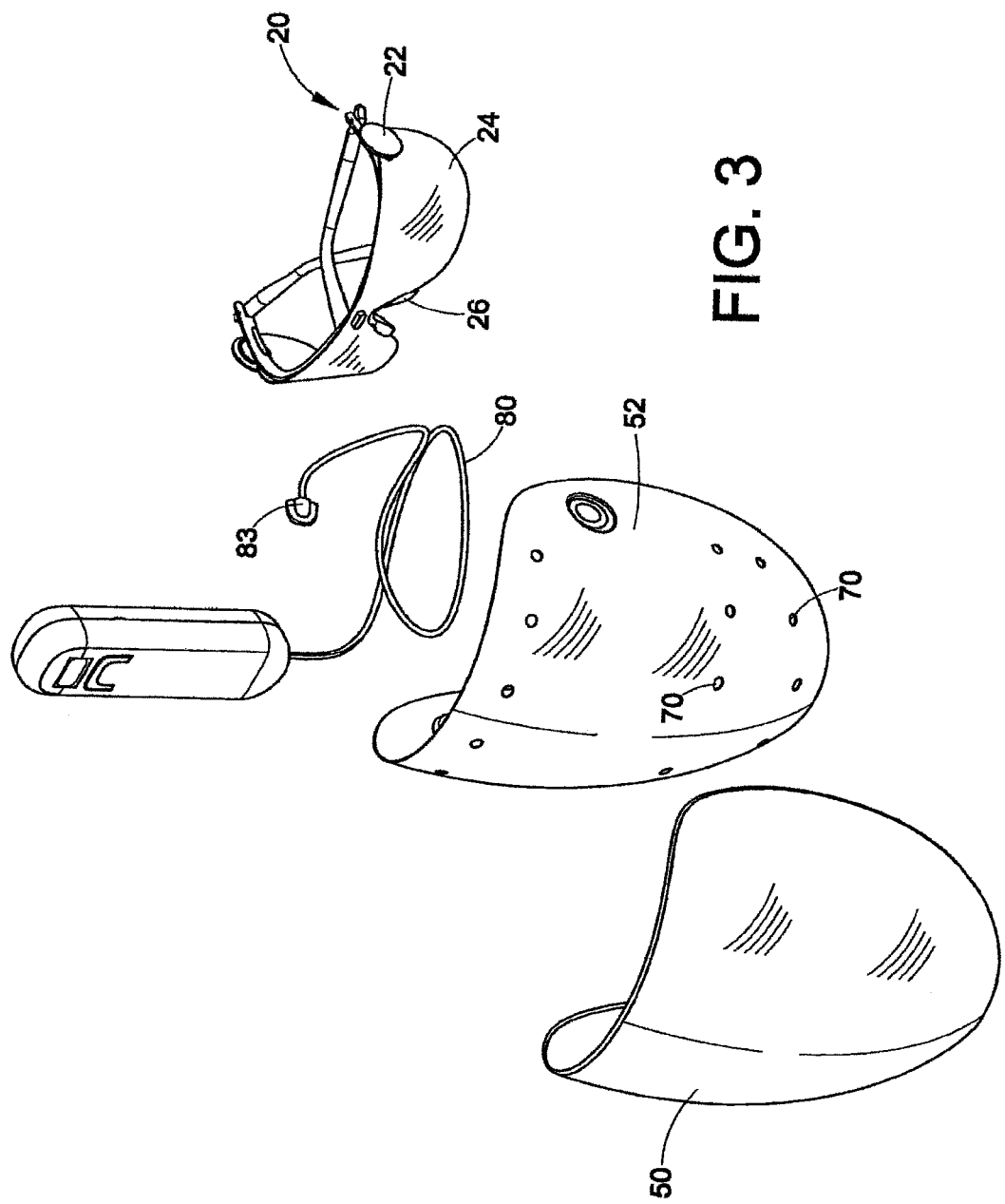
FIG. 3 is an exploded perspective view of FIG. 1.
Figure 4:
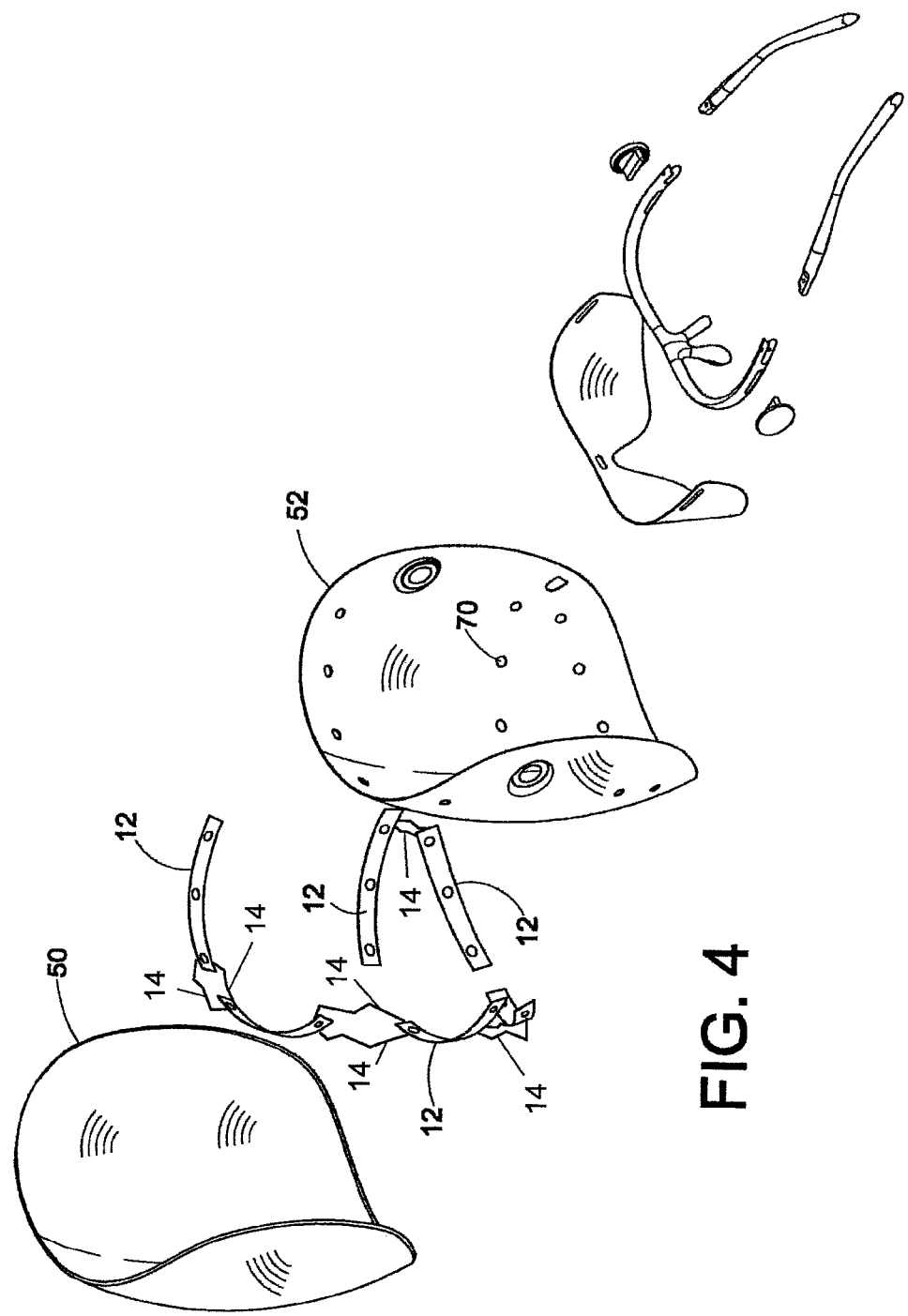
FIG. 4 is an exploded perspective view of FIG. 2.

With reference to FIGS. 3, 4, 6, 7 and 8 it can be seen that the wall structure 10 is comprised of an outer wall 50 and an inner wall 52. The outer wall is disposed furthest away from the treatment surface of the user, while the inner wall 52 is disposed closer thereto. The walls have a concave configuration in both horizontal and vertical directions and are constructed of a plastic material having a malleable rigidity so that the structure 10 can be bent and deflected slightly during use. The concavity comprises a multi-dimensional parabolic curvature for catching and reflecting the radiation back to the treatment areas. It is intended that the concavity is slightly smaller than the head of the user so that the mask has to be bent out when applied thereby providing a close but comfortable tightness on the user which will keep the assembly A in a desired position during use. The concavity also positions the therapeutic lamps or LEDs 12 in desired positions relative to the user. The spacing 54 between walls 50 and 52 receives the lamps 12 and circuitry 14 so that the lamps and circuitry are interposed between the walls for enhanced safety and convenience purposes. It can be seen that the spacing is diminished from the middle of the device towards the end portions 58, 60; however, the entire end perimeter of the assembly 10 is sealed as the walls come together. Such a mating seal is typically effected through a sonic weld arrangement. Alternatively, local sealing points (not shown) can be employed to assemble the walls together with spaced intermediate seals. Thus, the inner and outer masks have different radii of concavity but present an integral structure as far as the user is concerned. The outer wall 50 primarily functions as a support for the lamps 12 and circuitry 14. With reference to FIG. 4 it can be seen that the lamps are disposed on the wall 50 in a predetermined manner for radiating treatment areas most susceptible for the phototherapeutic treatment. A minimum number of lamps 12 are intended but still enough to provide effective therapy. Alternatively, the lamps could be fixed to the inner wall 52. Regardless of which wall supports the lamps, the lamps need to be properly aligned with apertures 70 to desired treatment areas.

Rather than placing a plurality of LEDs randomly, the subject LEDs are specifically minimized in number and disposed relative to the treatment areas and wall parabolic reflectivity to effect the desired therapy. More particularly, it can be seen that the individual lamps 12, and associated inner wall apertures 70, are disposed to treat the most common areas benefiting from the therapy. The present embodiments illustrate a placement pattern useful for skin acne treatment. Other placement patterns are certainly intended to fall within the scope of the disclosed embodiments. Here three LED strips are seen and would typically comprise two blue strips on the top and bottom of a middle red strip, as these frequencies are most useful for acne treatment. The subject invention may include only blue, only red, or any other mixed combination of LED or other radiant energy form pattern. The illustrated pattern would thus have intensified therapeutic effect on the jaw line, chin, cheek and forehead, but not the eyelids. Light sources can include LEDs, fluorescents, lasers or infrareds as an example. Such sources can vary in the form of the radiant energy delivery. Pulsed light (IPL), focused light (lasers) and other methods of manipulating light energy are encompassed within the present embodiments. Other methods of light emission may comprise continuous, pulsed, focused, diffuse, multi wavelength, single wavelength, visible and/or non-visible light wavelengths.

The inner wall 52 is comprised of a smooth seamless reflective surface facing the treatment area and includes a plurality of apertures 70 matingly aligned relative to the lamps so that the lamps can radiate the therapeutic light 57 through the apertures 70. Accordingly, the LEDs 12 are recessed relative to the inner wall 52 to preclude contact with the treatment surface and to make it very difficult for the lamps themselves to be in any way contacted by the user. Such an assembly results in a controlled communication of radiating therapy in a manner to impart a predetermined cone of therapeutic light on to a treatment area. The apertures are disposed relative to desired treatment areas and wall parabolic configuration for even light distributions across the treatment area. A combination of such a controlled cone of light, predetermined disposition of the lamps themselves on the platform, an inner reflective surface on the inner wall 52, and a controlled positioning of the assembly relative to the treatment area via a platform position relative to contact areas of the nose and the ears, presents an assembly which presents a highly predictable distributive pattern of the light (predetermined cones of light per light source), thereby minimizing the number of lamps 12 that need to be included for effective treatment.

Figure 2:
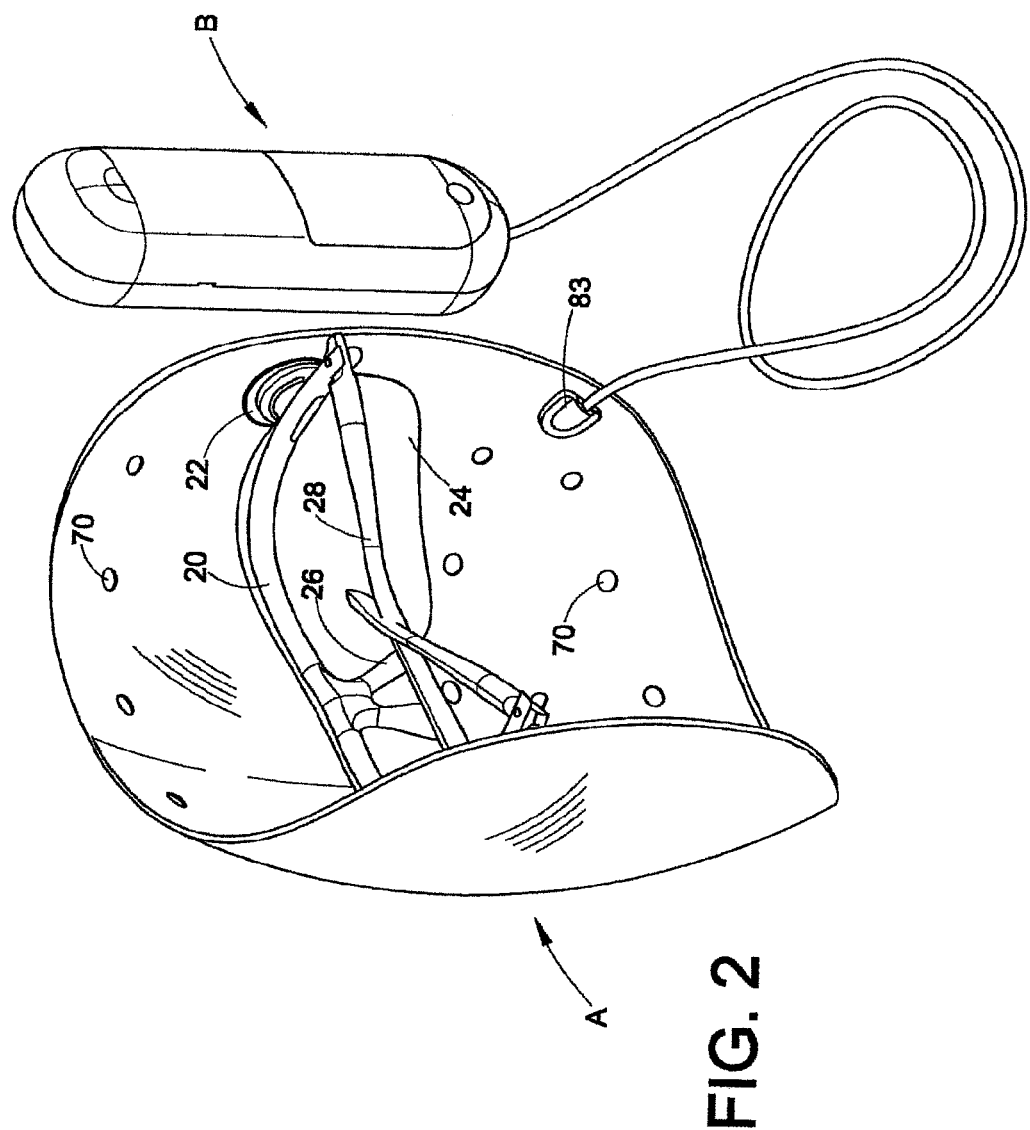
FIG. 2 is another perspective view of the device of FIG. 1.

With reference to FIGS. 2, 3 and 4, one embodiment comprises a support frame essentially comprising eyeglass frames as the associated support structure for the platform 10. Interchangeable lenses 24 can be used to adjust the level of protection afforded by the lenses or their relative shape. Although not shown therein, telescopic temple arms 28 may telescope for better sizing relative to the head size of the user. Formable ear latches can also be included as part of the temple arms. Alternatively, the arms could include a head strap. The pivotable joints 22 allow the wall structure to pivot relative to the frames so that a user may adjust light intensity relative to a treatment area by moving the layers closer or farther away. As noted above, the platform 10 is flexible with a concave parabolic bias, but still has a malleable rigidity. When the frame 10 is received on the user, it is disposed to expand the platform parabolic bias to form a match to the size of the user. Eyeglass frame reference contact points of the user may comprise the nasion area, the nose bridge and the ears of the user. Alternatively, the support frame can comprise a goggle and head strap configuration relying on the nasion area.

Figure 5:
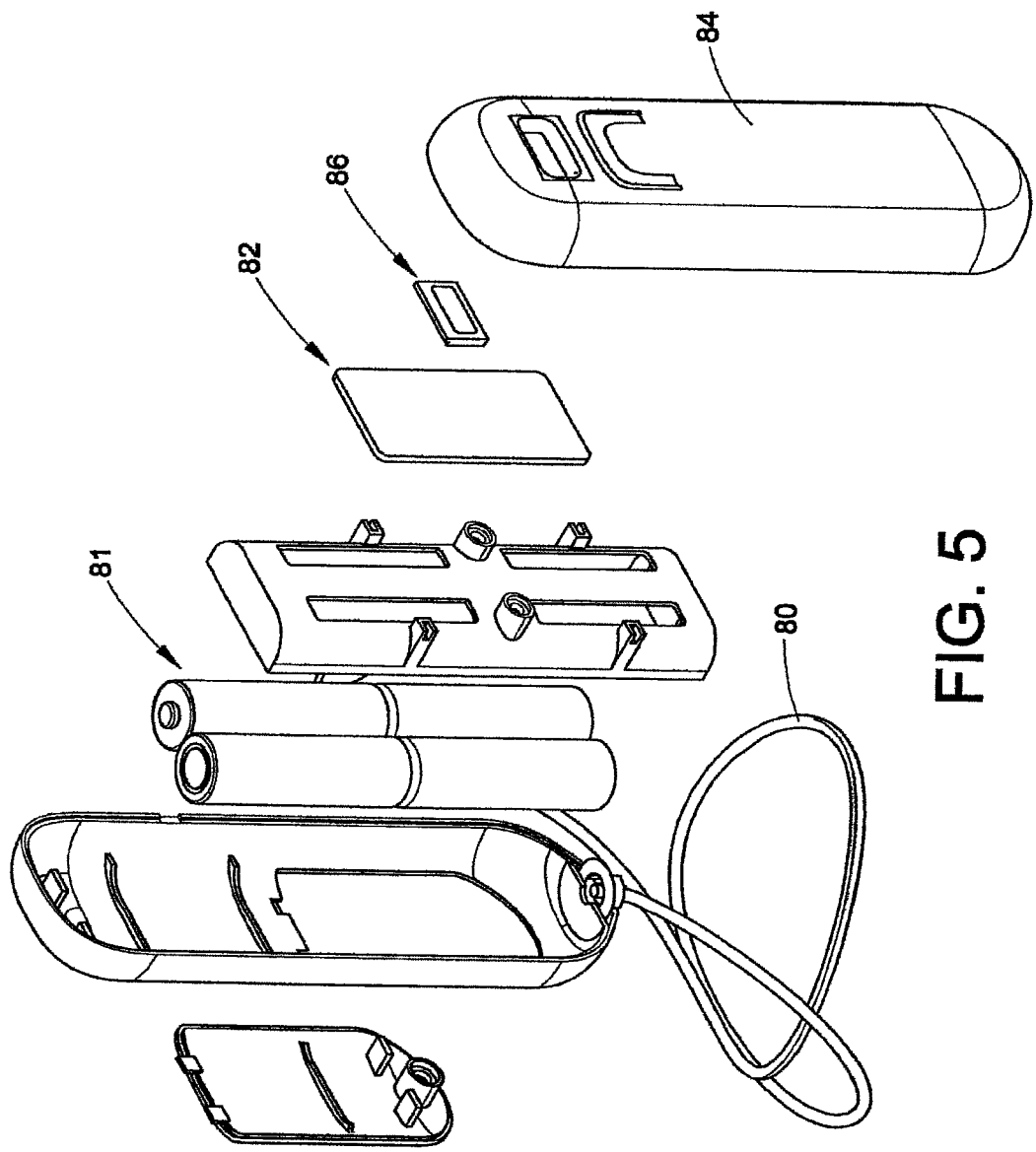
FIG. 5 is an exploded perspective view of the controller B.
Figure 6:
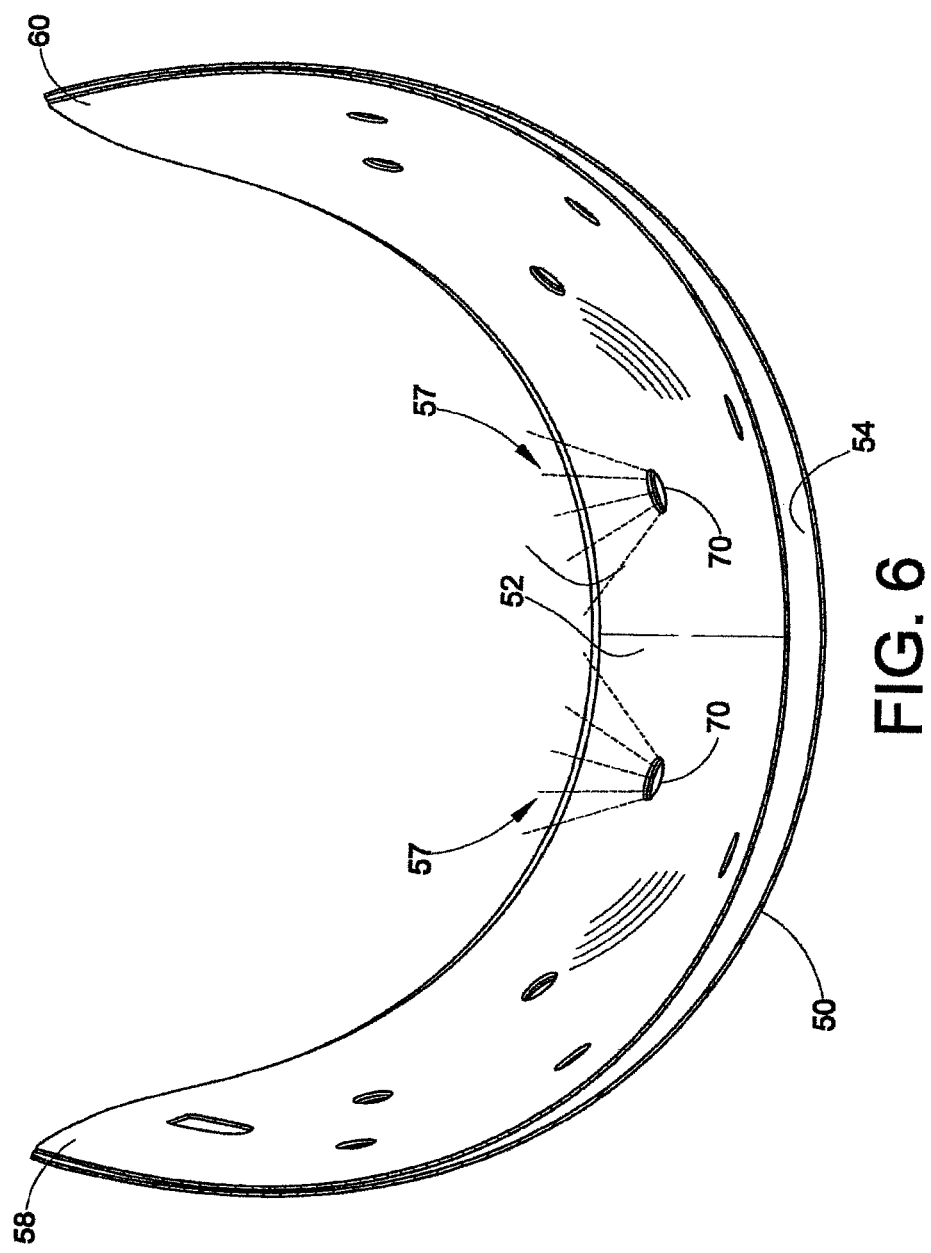
FIG. 6 is a cross-sectional view showing a two-wall structure of the embodiment of FIG. 1 wherein an inner wall includes light apertures aligned with the LEDs for communicating the therapeutic light to the user.
Figure 7:
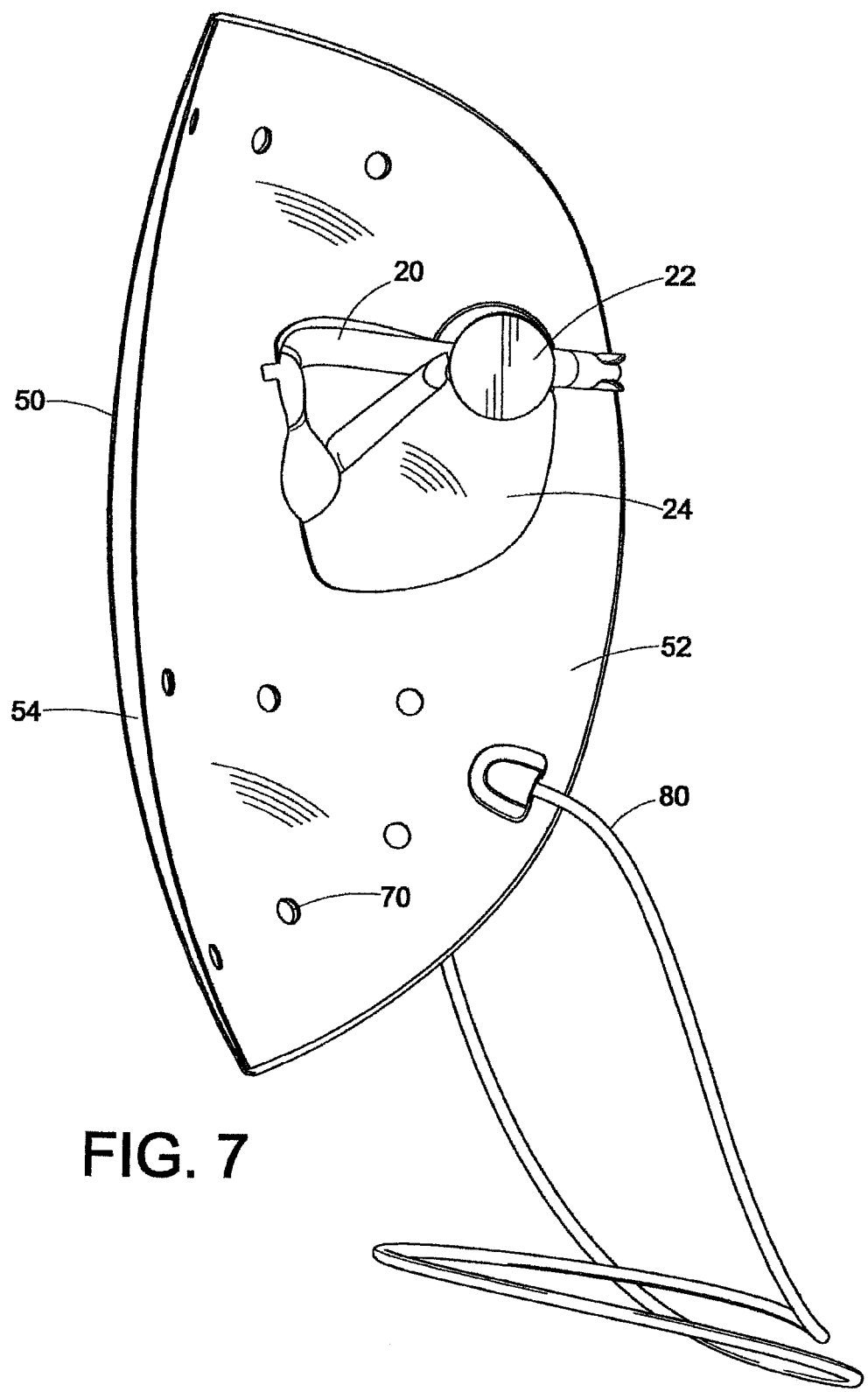
FIG. 7 is a second cross-sectional view taken along a vertical center-line.
Figure 8:
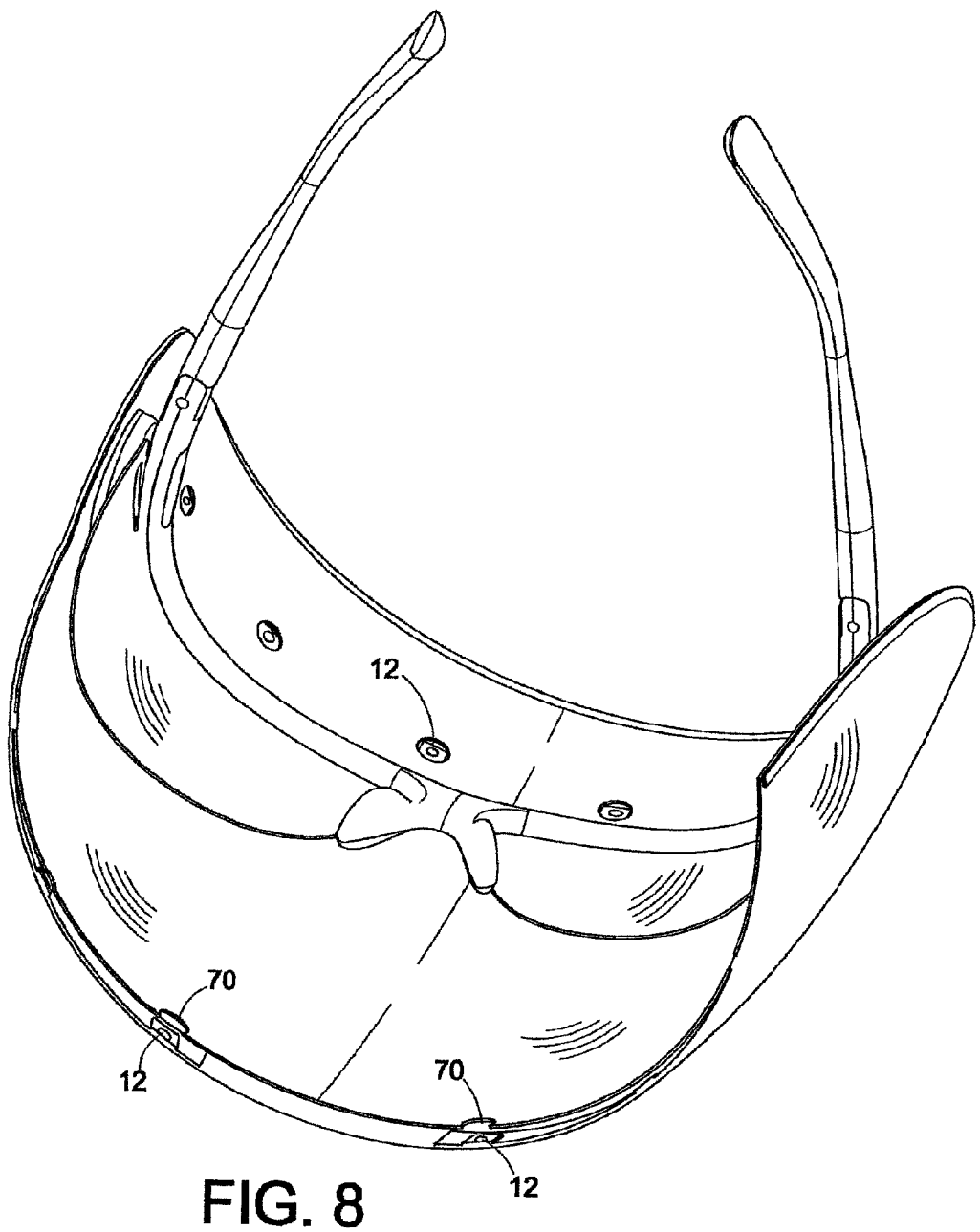
FIG. 8 is a partial cross-sectional perspective view illustrating disposition of recessed LED lamps relative to inner wall apertures.

Battery pack B (FIG. 5) holds the supply batteries 81 and processing controller 82 that is in electrical communication with the lamps through wire 80. The wiring between connectors 83 and LED strips 12 is not shown to avoid drawing clutter but is contained between walls 50, 52. The battery pack will include an on-off switch 84 and a user interface 86. The processing controller 82 may include a variety of control systems indicating device usage to the user. Such a system would be a counter. The user interface may comprise a display for a variety of useful information from the controller control systems to the user, such as a count of the number of times of usage and communication that the device has been used enough times such that the LEDs themselves have degraded and a replacement is recommended for the therapy.

Figure 11:
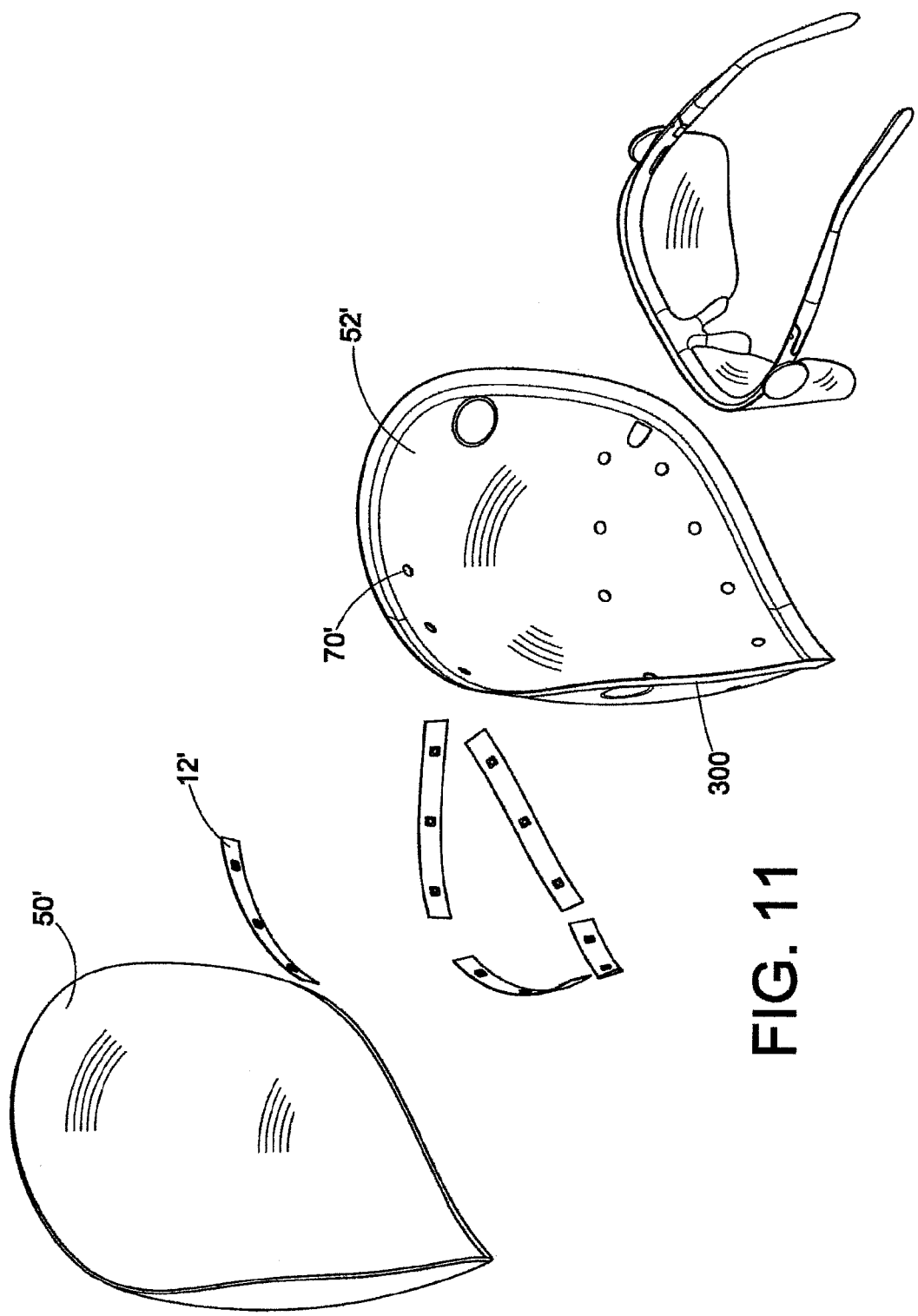
FIG. 11 is an exploded view of an alternative embodiment wherein the mask walls are spaced by a flange.
Figure 12:
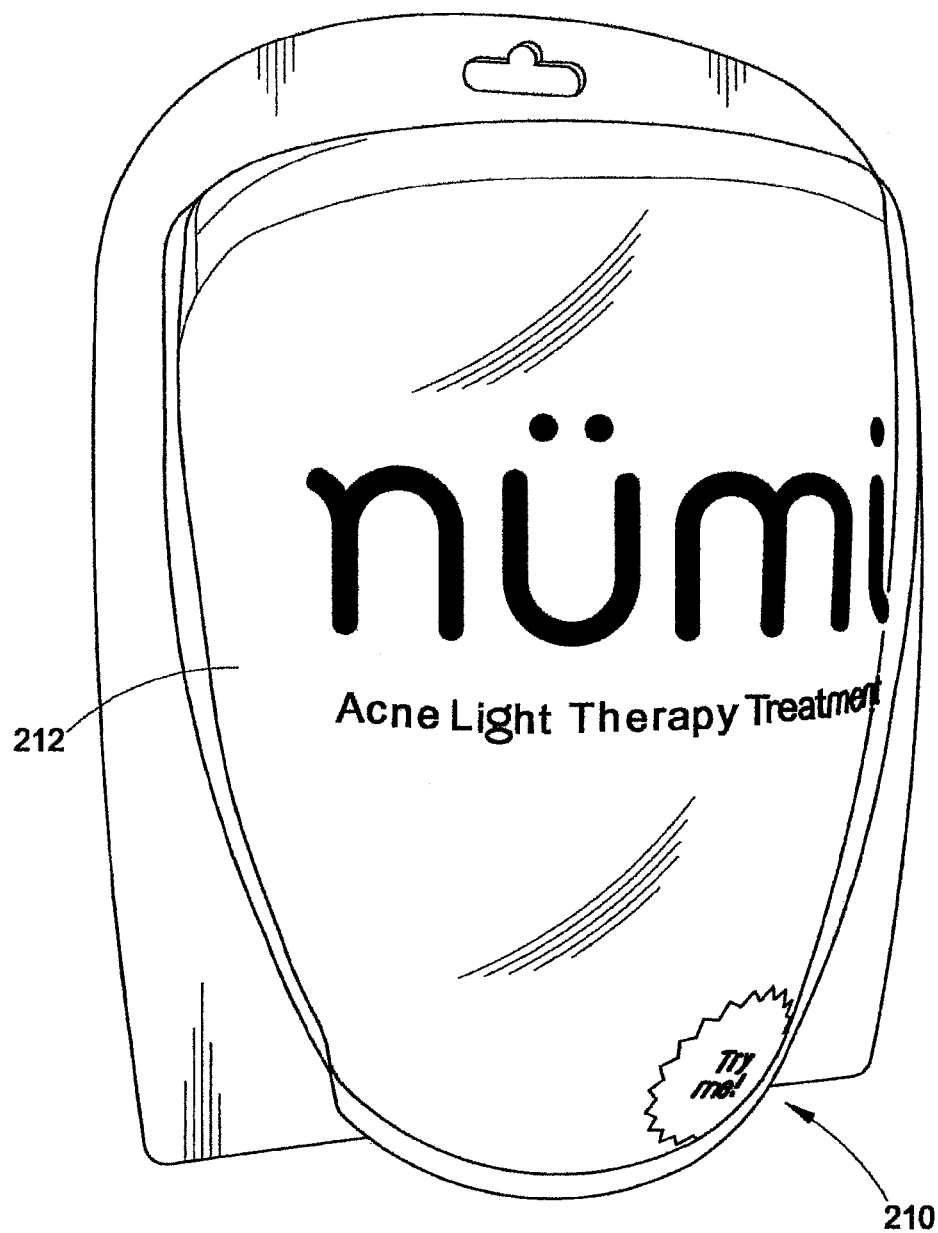
FIG. 12 is an embodiment of a packaging assembly containing the device of FIG. 1.

"Try-me packaging", FIGS. 11 and 12, presents a demonstrative use opportunity to a potential user while still packaged. The subject embodiments further include a packaging assembly 210 containing the device wherein a switch S1 (not shown) for operating the lamp assembly has a multi-position effect functionality including an on-mode, an off-mode and a try-me mode. The try-me mode is accessible while the lamp assembly is contained in packaging for displaying lamp operation to a user. The packaging includes a clear or translucent cover 212 over the device A. A try-me time-out circuit is included for limiting the try-me display time of lamp operation, such as, for example two seconds. Lamp on-time as measured by the counter is segregable from the try-me mode so that try-me usage will not affect dosage count of the device for actual therapy. It is assumed try-me usage time will be negligible relative to a dosage use time.

The subject devices include multiple benefits to the user in a wearable hands-free device with a remote battery pack. The device is properly positionable in a relatively automatic way with minimal human touch by exploiting user reference contact points, and is particularly hand-free during use. No sharp or hot surfaces are engageable by the user. A smooth seamless surface faces the user and is properly spaced from the treatment area to provide enhanced ventilation and minimal discomfort during treatment.

Figure 13:
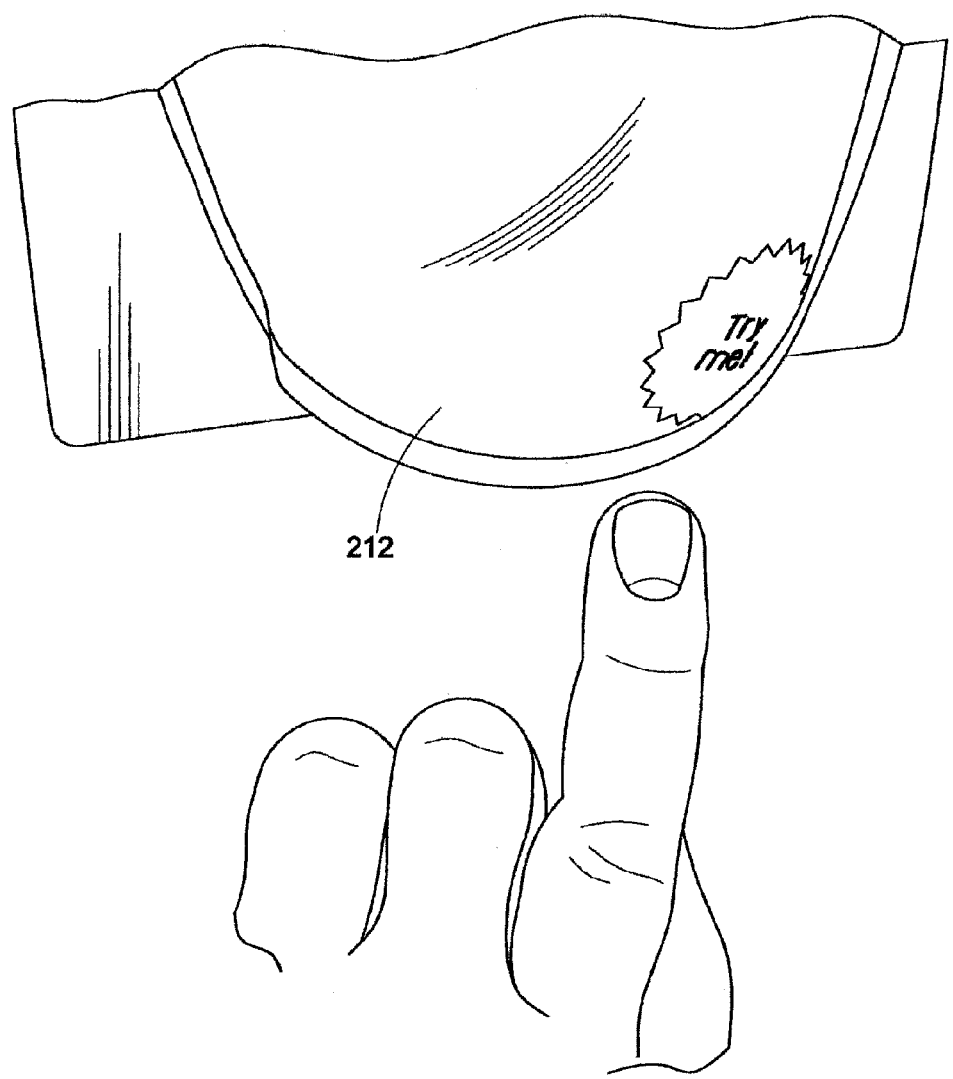
FIG. 13 illustrates a try-me feature of the packaging of FIG. 11 wherein a user can view a sample operation of the device.
Figure 14:
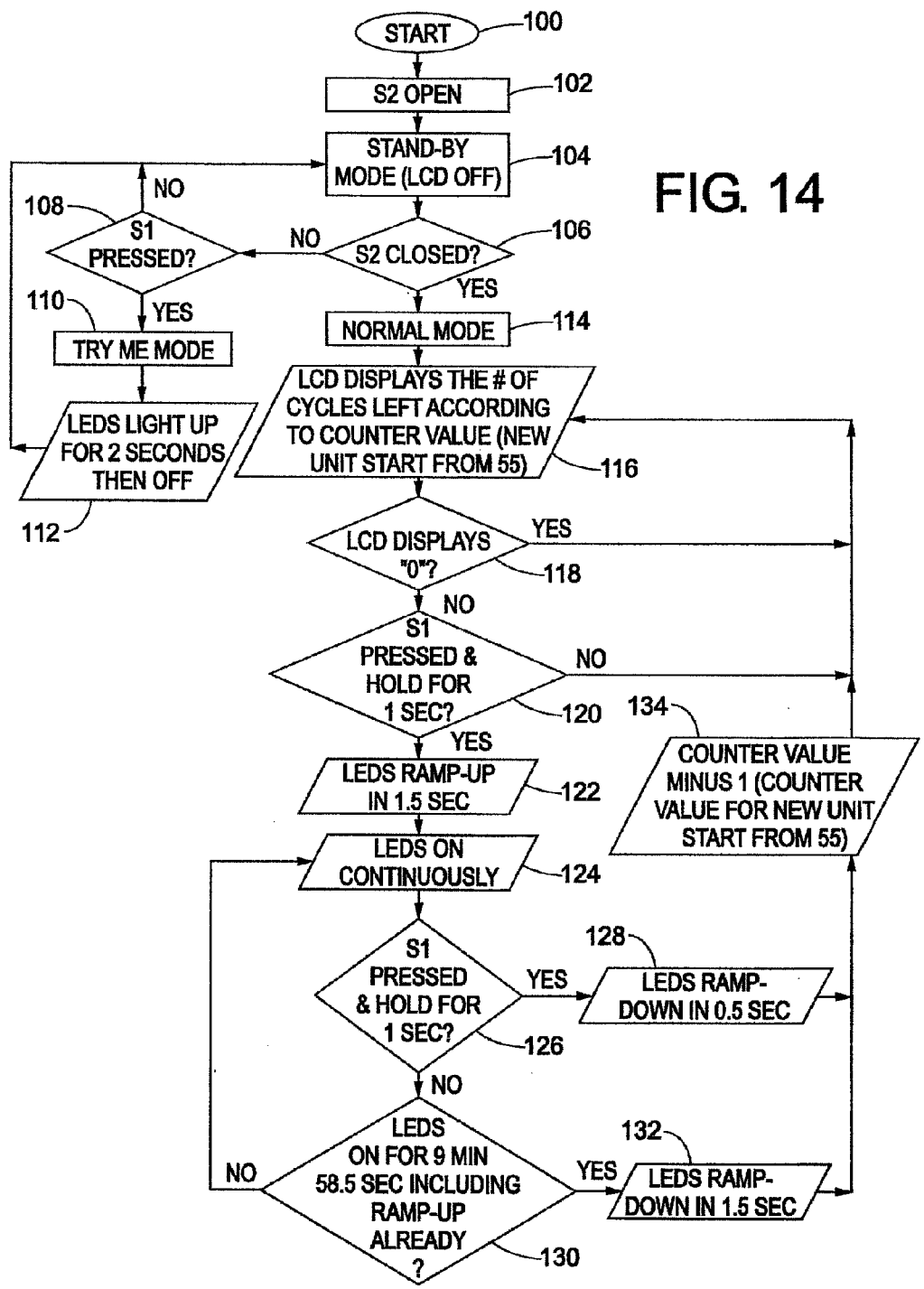
FIG. 14 is a flowchart of operational device control.

With particular reference to FIG. 13, a flowchart illustrating an operational embodiment of a device control is illustrated. The device visioned as operational by FIG. 10 includes two switches, S1, S2, at least one of which are required to be closed to communicate energy from an energy source to the therapeutic lamps. S2 is a safety switch which is open when the device is in sales packaging so that only the "try-me" mode is enabled when S2 is open. After removal from the packaging, S2 can be closed and the device can be operated in a normal mode. Accordingly, after start 100, and in a situation when S2 is opened 102, such as when the device is still within the packaging, the system will remain in a stand-by mode wherein the GUI interface (such as an LCD) is off 104. If S2 remains closed 106 but S1 is pressed 108 (e.g. FIG. 12), then the device can enter the "try-me" mode 110 wherein the LEDs will light up for two seconds, then turn off 112. Such a "try-me" mode operational demonstration to a user while the device is in a packaging communicates to the user actual operation and can assist in a decision to purchase, or have a better understanding of how the device operates. If the device is removed from the packaging, and S2 is closed, the device will enter normal mode 114 wherein the GUI will include an LCD displaying the number of cycles left according to a counter value. Note that counter value 134 is not affected by any try-me sampling operation.

In one embodiment, the unit will count down from 55 to 1, as 55 uses is deemed to be enough to diminish enough LED efficiency from the peak operational mode of LEDs when they are used as the therapeutic radiant lamps. Accordingly, upon a user picking up the device, they will immediately know how many cycles are left for acceptable and recommended operation of the device from 55 more uses all the way down to 0 118. If the display shows a count greater than 0, and the user is interested in a therapy session, the user will turn the unit on by pressing S1 120 wherein the LEDs will ramp up to radiant operation 122 in approximately 1.5 seconds and then will radiate continuously 124 until either the user desires to turn off the unit by again pressing S1 126 so that the LEDs can ramp down 128 or until a therapy session has timed out 130 such as for remaining radiant for approximately ten minutes. After completing an appropriate run time of a therapy session, the LEDs will ramp down 132 and the GUI display to the user will subtract 1 from the counter value 134.

Figure 9:
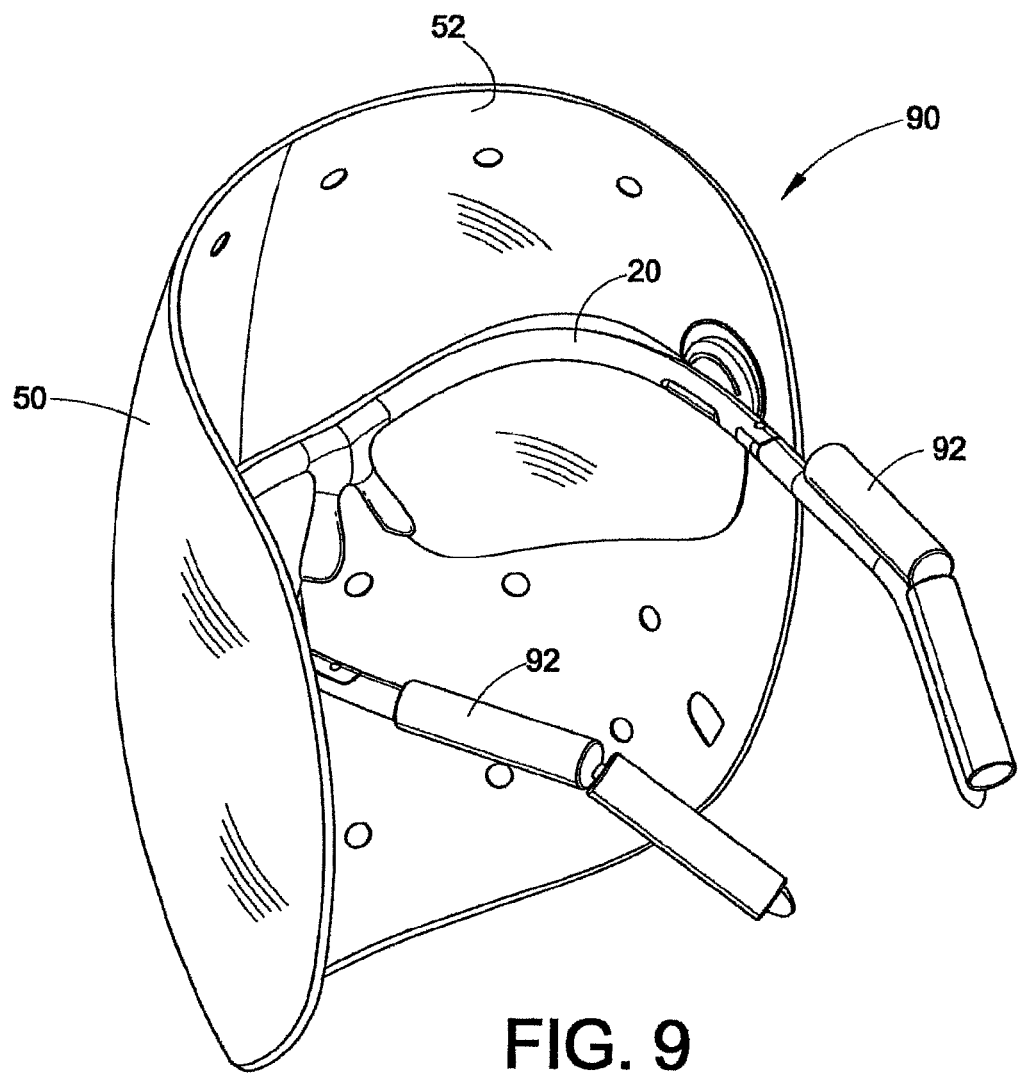
FIG. 9 is a perspective view of an alternative embodiment wherein the power supply and control circuitry are integrally formed with the mask assembly.
Figure 10:
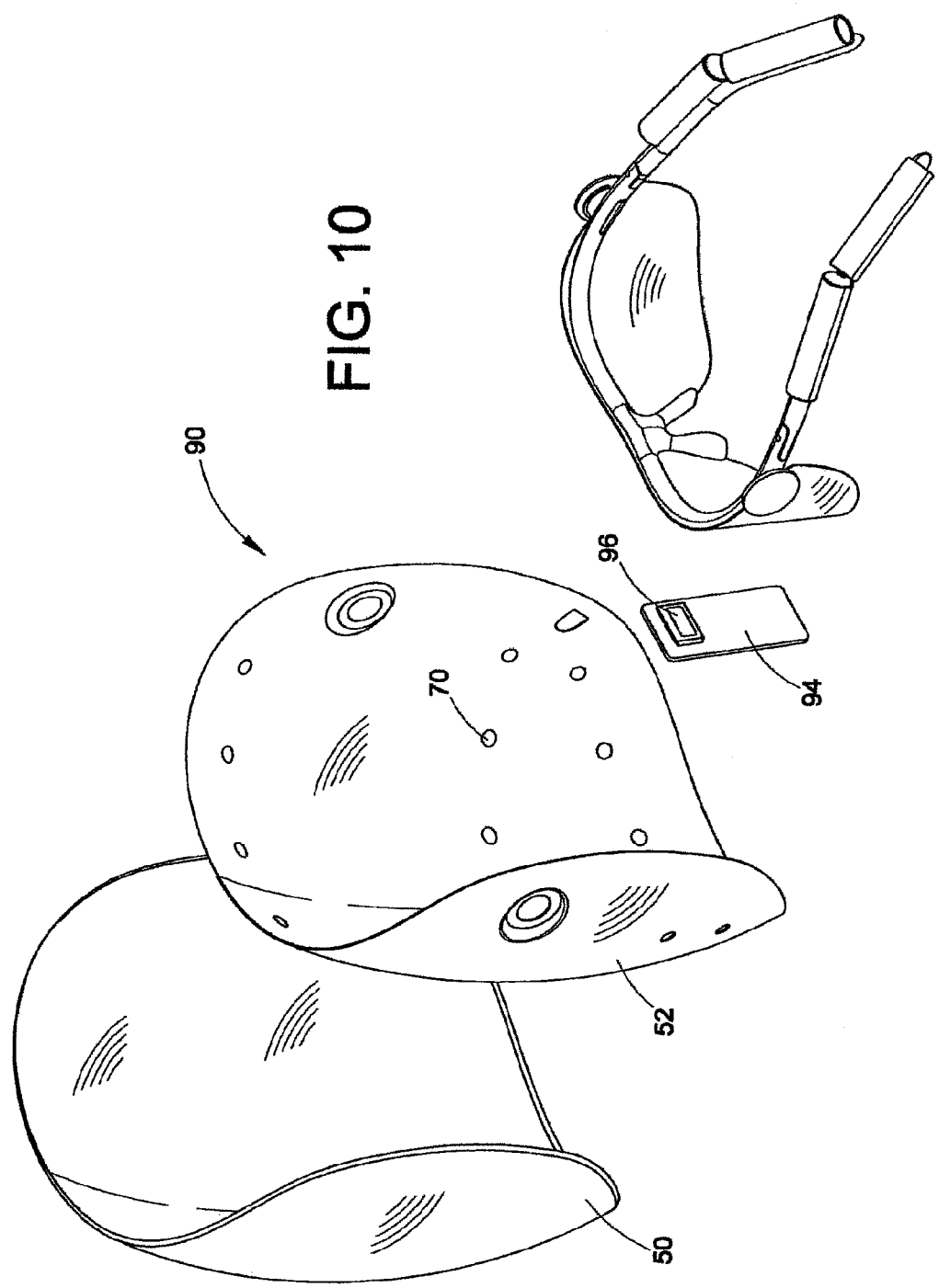
FIG. 10 is an exploded view of the device of FIG. 9.

With reference to FIGS. 9 and 10, an alternative embodiment is shown wherein a controller B is eliminated and the energy source and processing control are all integrally assembled in the device 90. In this case, the platform 20 and walls 50, 52 remain substantially the same as per the FIG. 1 device. However, the energy source such as batteries 92 are disposed as part of the eyeglass temple arms wherein wires provide energy from the batteries 92 to the LEDs through the hinge points of the frame 20 and into the spacing 54 for ultimate connection to the LEDs themselves. The controller 94 including LCD display 96 is also housed behind the reflective wall 52 relative to the user, which wall 52 can include a relatively small cutout (not shown) for the screen 96.

The embodiment of FIGS. 9 and 10 is thus even more compact than the embodiment of FIG. 1, and more hands-free therefrom, as it eliminates the need to somehow manage the controller B during operation.

FIG. 11 shows yet another alternative embodiment wherein the outer wall 50' and the inner wall 52' are not spaced by being configured with different curvatures. Rather, the walls 50', 52' have the same curvature, but the inner wall 52 has an off step 300 depending from the wall perimeter to form a flange raised from the surface of the wall 52' towards the outer wall 50' to effectively form a spacer between the two. In one embodiment, the flange 300 is about 8 millimeters wide, continues around the entire perimeter of the wall 52' and is about 0.5 millimeters thick for effecting the desired spacing between the inner and outer walls. In this embodiment the flange 300 is part of the inner wall 52', and as in the foregoing embodiment, both walls are vacuumed formed plastic, either PET or PVC. The assembly of FIG. 11 can be sonic welded, glued, or adhered with double-sided adhesive. Alternatively, a plurality of intermediate sealing points (not shown) could be used instead of a continuous seal. In this embodiment it can be seen that there is an alternative number of LEDs 12' opposite the forehead portion of the assembly relative to the user so that the number of apertures 70' and LEDs 12' are reduced from the foregoing embodiment from eighteen to fifteen. Either number of LEDs is a viable implementation of the desired therapy, although the other componentry of the assembly FIG. 11 is substantially the same as that shown in the foregoing figures.

Another alternative embodiment from the device shown in FIG. 1, etc., includes disposition of a transparent flexible polymer sheet (not shown) incorporating working LED lights between outer wall 50 and inner wall 52. Such a configuration would comprise the polymer film being coated with a transparent thin layer of carbon nanotubes in a specific configuration to act as the wire pathways to connect LED lights. The polymer would protect the LEDs from user contact. Such protective polymers are available under the Lumisys® brand.

Yet another alternative embodiment includes such a transparent flexible polymer sheet wherein a reflective film is applied on top of the flexible polymer sheet including cutouts opposite the LEDs for allowing the radiant light to communicate through a reflective area in a manner as shown in the relationship of FIG. 4 between the LEDs' 12 inner wall 52 through aperture 70. This arrangement may also include a flexible outer wall 50 on the other side of the flexible polymer sheet to provide malleable rigidity to the film, reflective coating assembly.

Yet another alternative embodiment includes a plurality of sensors (not shown), such as temperature or radiant energy sensors, disposed relative to inner wall 52 to monitor radiant energy exposure of a user during therapy. If such exposure is deemed inappropriate for any reason, sensing thereof is recognized by controller B and the therapy can be halted.

Figure 15:
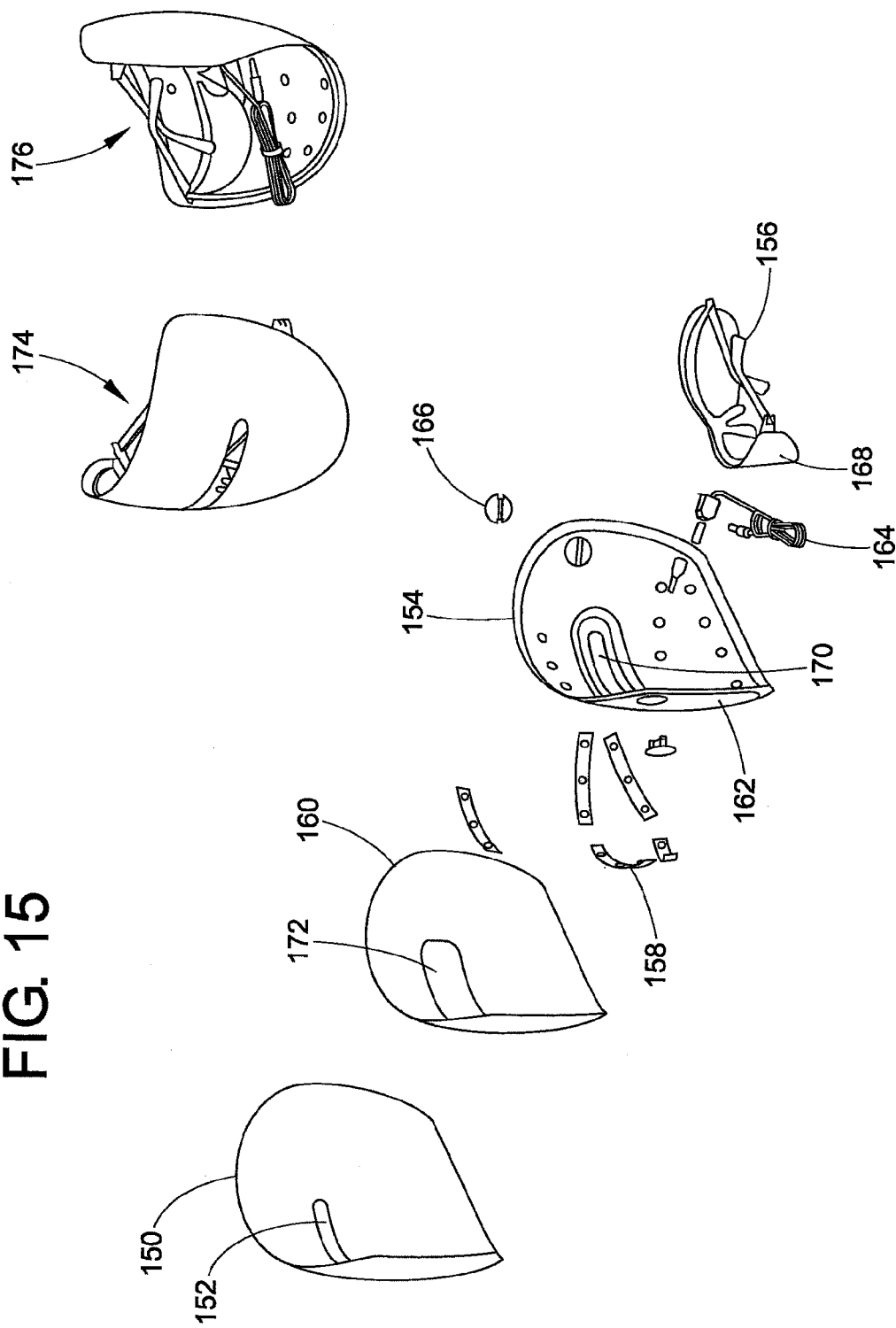
FIG. 15 is an exploded view of an alternative embodiment including a see-through slot and a third light absorbing layer.
Figure 16D:
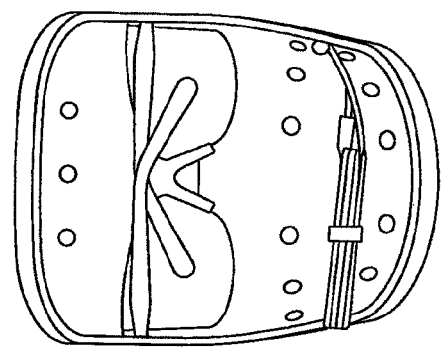
FIGS. 16A-16D are elevated views of the assembled device of FIG. 15.
Figure 16C:
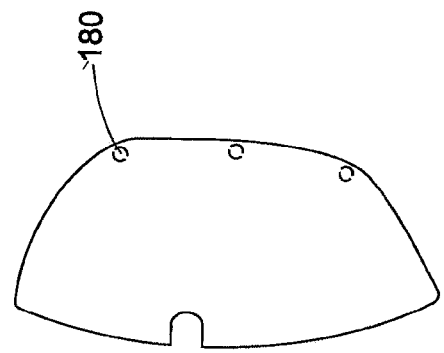
Figure 16A:
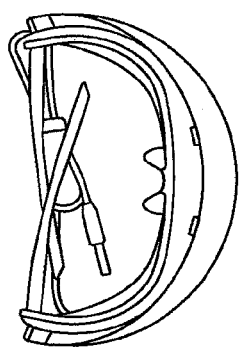
Figure 16B:
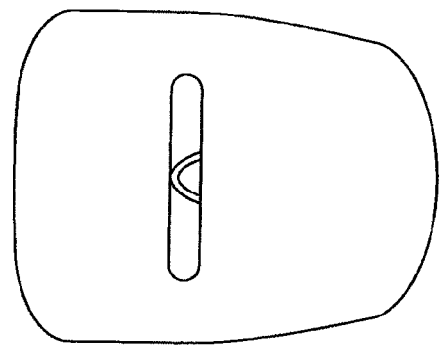

FIG. 15 shows yet another alternative embodiment including an outer shield 150 including a see-through slot 152, an inner reflective shield 154, and eyeglass assembly 156, and LED strips 158. These elements are substantially similar, but for the see-through slot 152 and corresponding aligned slots, as the foregoing embodiments. Alternatively, this embodiment includes a third layer 160 intermediate the outer shield 150 and the inner shield 154. Layer 160 preferably comprises a thin opaque black plastic sheet which serves to absorb or block out lamp radiation and eliminate all light leakage from the front of the mask, i.e., out through the outer shield 150. Layer 160 is preferably affixed to the inside of the outer layer 150 and then the LED strips are affixed to the layer 160. The strips 158 still remain recessed relative to the inner surface 162 of the inner shield 154 for the benefits noted above. FIG. 15 also shows a controller assembly cable 164 and an eyeglass assembly mounting post 166. The eyeglass assembly lenses 168 are tinted but do not preclude a user to see through the inner shield slot 170, the third layer slot 172 and the outer shield see-through slot 152. The aligned slots 152, 170, 172 comprise a continuous viewing opening that is an integral part of the mask. A layer 160 is sized to provide perimeter spacing from the outer perimeter of the outer shield 150. When the unit is operating and the LEDs are illuminated, this provides a perimeter illumination to an observer of the user which not only communicates that the unit is in operation but provides an aesthetically pleasing appearance.

In one embodiment the LED strips 158 are preferably attached to the intermediate third layer 160 by being received in corresponding pockets (not shown) in the layer 160. Alternatively, they can be adhesively applied to the layer 160. The wires between the strips 158 are very thin and just rest between the middle layer and the inner shield 154, i.e., no special wire routing. There is accommodation for the main cable and strain relief—leading to the first LED strip. The whole middle layer assembly fits into the chamfered recess in the inner shield 154, and there are locating points top/bottom and left/right. This is secured with double-sided tape. The middle layer/LED strips/inner shield assembly is completed by the outer shield 150 (also by double-sided tape). There are several sonic welds 180 (FIG. 16) that permanently secure the layers together. Assembled perspective views 174, 176 are shown. FIGS. 16A-16D illustrate elevated views of the embodiment of FIG. 15 when assembled.

Figure 17:
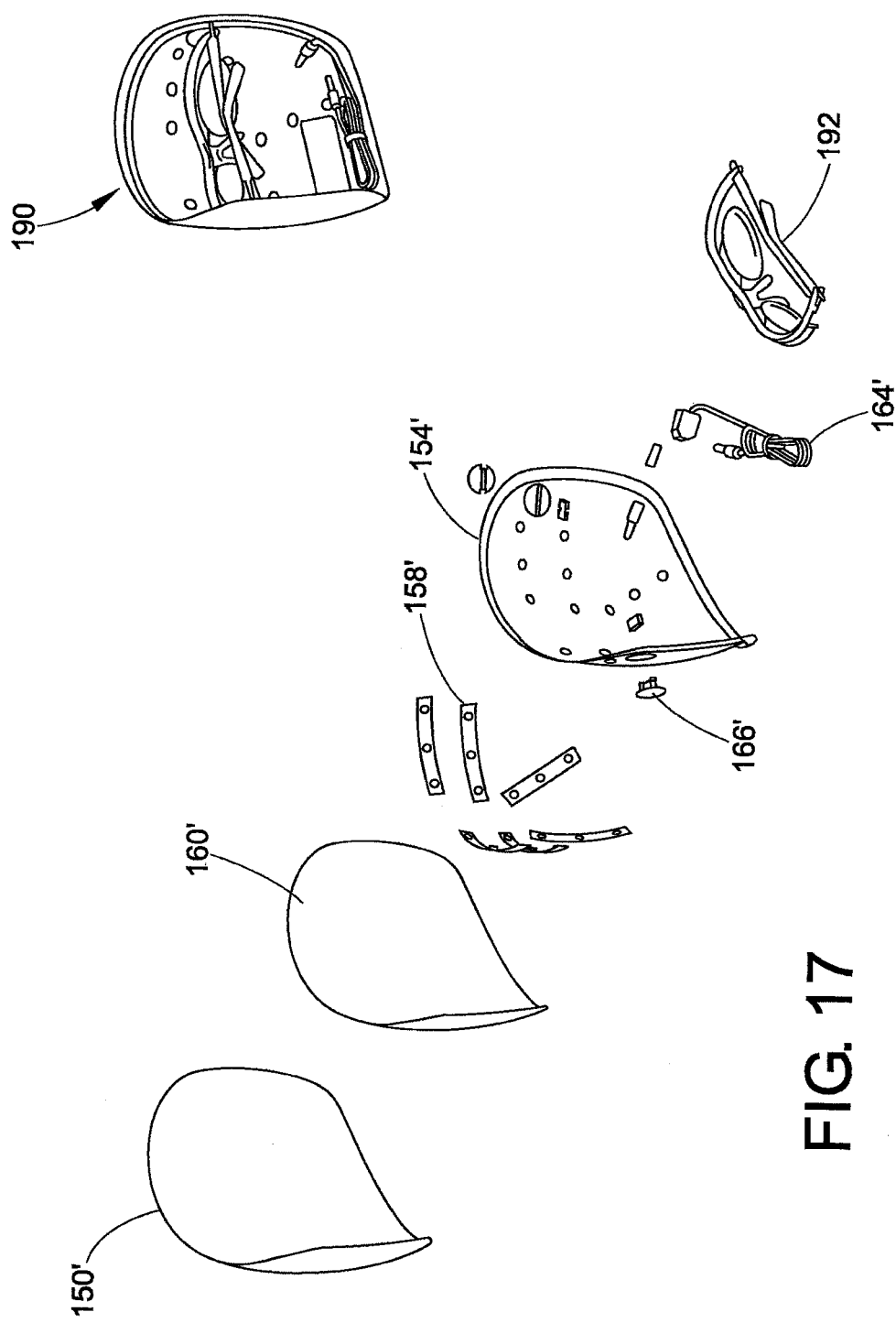
FIG. 17 is an exploded view of an alternative embodiment including eye protecting goggles.

FIG. 17 is yet another alternative embodiment which differs from the embodiment of FIG. 15 in that the see-through slots 152, 170, 172 have been eliminated and the eyeglass assembly 190 no longer has tinted lenses, but radiant light blocking goggles 192. Like elements from FIG. 15 are same numbered and primed. In this embodiment, the eyes are to be protected from any of the radiant energy emitted by the lamps. Such an embodiment is particularly useful for a phototherapeutic treatment of red and infrared light for an anti-aging therapy. A red light evens skin tone and reduces roughness. Infrared light reduces the appearance of fine lines and wrinkles. However, whatever radiant energy may be employed, the goggles 192 completely shield the eyes from the radiant energy.

Figure 18:
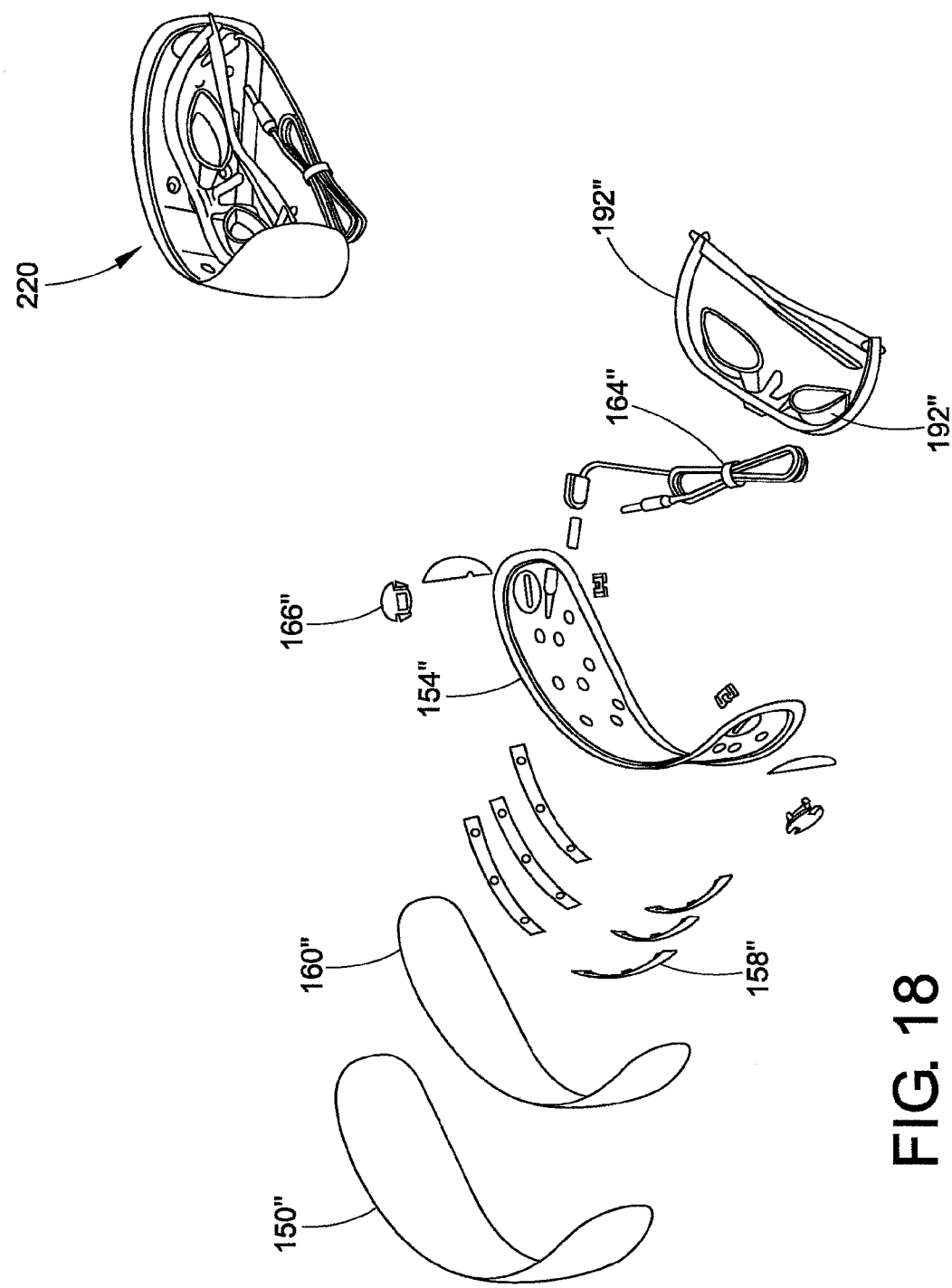
FIG. 18 is an exploded view of an alternative embodiment having a mask sized for applying the LED therapy to the eye area.

FIG. 18 is yet another embodiment where the mask assembly 220 is sized to only treat the eye area of a patient so that the assembled mask is much smaller than that shown in FIG. 17. The LED strips 158" are disposed in a different arrangement from that FIG. 16 but the other elements are essentially the same including the protective goggles 192".

Figures 19A, 19B:
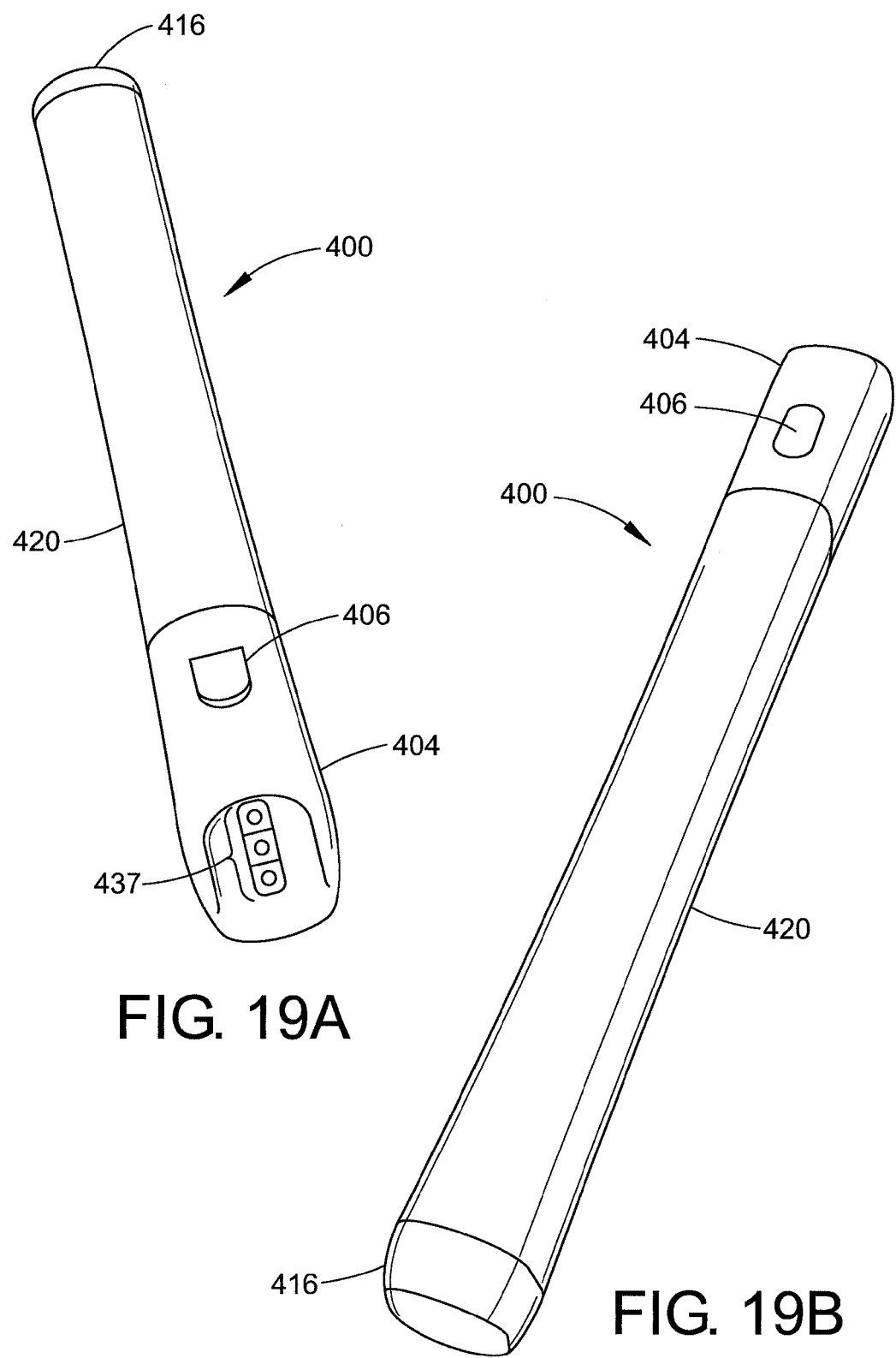
FIGS. 19A and 19B are perspective views of a light therapy spot applicator according to an exemplary embodiment of this disclosure.

With reference to FIGS. 19A and 19B, illustrated are perspective views of a light therapy spot applicator 400 according to an exemplary embodiment of this disclosure. In addition, FIGS. 20-24 provide further details of the exemplary embodiment shown in FIGS. 19A and 19B. While the description that follows provides details of a light therapy spot application for acne spot treatment, it is to be understood that other skin ailment treatments are within the scope of this disclosure, for example, but not limited to other spot blemish treatments.

As shown in FIGS. 19A and 19B, the disclosed light therapy spot applicator 400 includes an elongated tubular structure 420, LEDs 437 to deliver light therapy spot treatment, a shroud 404 which covers circuitry/control of LEDs and provides an inclined treatment applicator surface, a control slide switch and a foot 416. To operate the light therapy spot applicator 400, a user operates the button switch 406 to turn on the device and places the LED end of the device directly against the desired treatment area. A concave face of the shroud 404 protects the user treatment area from direct contact with LEDs 437 and the concave face of the shroud 404 provides reflectivity of radiation from the user treatment area back to the user treatment area. The inclined concave face of the shroud 404, relative to a longitudinal axis of the tube 420, provides an ergonomic design for ease of use resulting in effectively and efficiently treating a facial spot treatment area, such as acne.

Figure 20A:
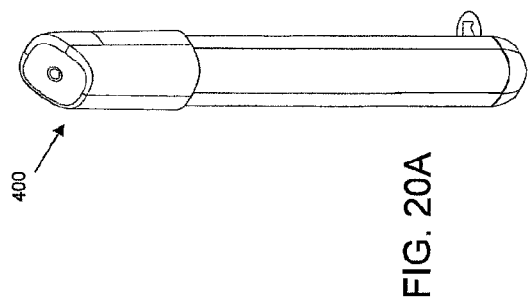
FIG. 20A is another perspective view of a light therapy spot applicator according to an exemplary embodiment of this disclosure.
Figure 20B:
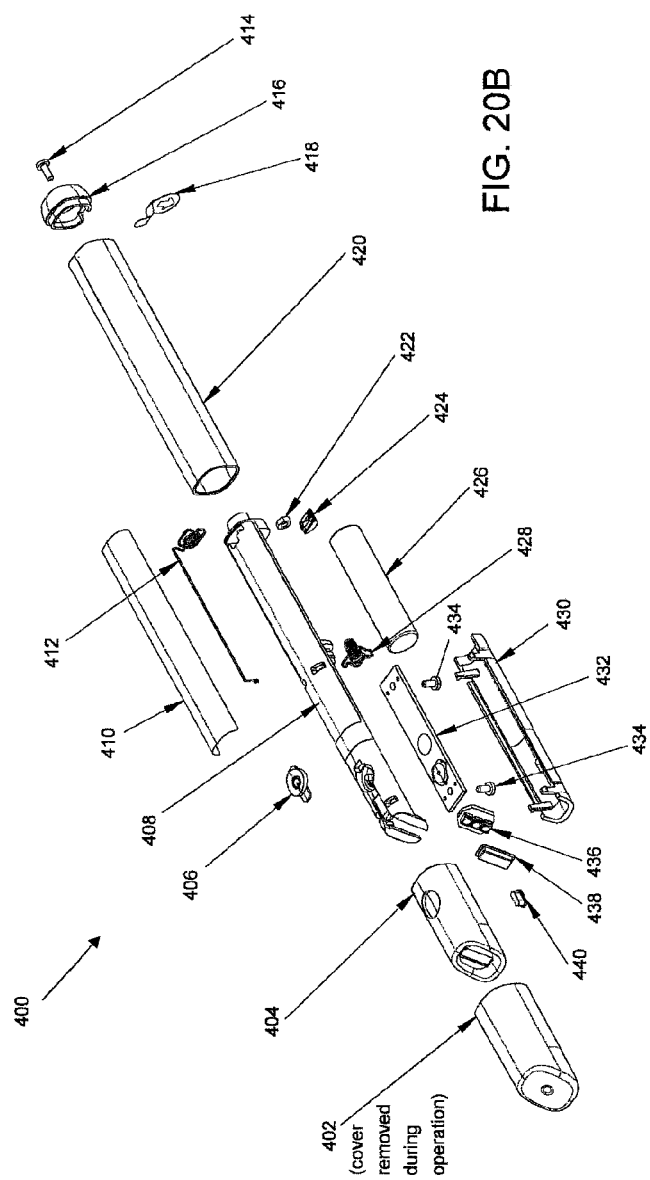
FIG. 20B is an exploded view of the light therapy spot applicator shown in FIG. 20A.

With reference to FIGS. 20A and 20B, FIG. 20A is another perspective view of a light therapy spot applicator according to an exemplary embodiment of this disclosure and FIG. 20B is an exploded view of the light therapy spot applicator shown in FIG. 20A.

As shown, the exemplary light therapy spot applicator 400 includes a cover 402, a shroud 404, a button switch 406, a frame 408, a label 410, a positive battery connection 412, a fastener 414, a foot 416, a battery pull tab 418, a tube 420, a nut 422, a nut cover 424, a battery 426, a negative battery connection 428, a frame cover 430, a main PCB (Printed Circuit Board) 432, a fastener 434, a LED PCB 436, a LED cover 438 and a shroud rivet 440.

With reference to FIGS. 21A-21F, illustrated are various views of the light therapy spot application shown in FIGS. 20A and 20B.

As can be seen in the figures, the face 405 of shroud 404 is substantially concave shaped and provides a radiant energy communication area for the LEDs 437 to provide light therapy, i.e., radiation therapy, to a user treatment area. In addition, a reflective surface of the concave shaped shroud enhances the efficacy of the device by reflecting radiation from the user treatment area, as well as radiation emitted directly from the LEDs, back to the user treatment area. Furthermore, the concave shroud includes a raised or protruding surface which enables a user to place the shroud face directly on a treatment area without any direct contact of the LEDs 437 with the user treatment area, i.e., skin. As previously described, an inclined or angularly offset face relative to the longitudinal axis of the tube 420 and frame 408 provides an ergonomic design for ease of use. It is to be understood that various angular offset angles can be used and include angular offsets less than 90 degrees and greater than 0 degrees relative to the longitudinal axis of the elongated overall structure of the light therapy spot treatment device. For example, from 15 degrees and 75 degrees, from 25 degrees to 65 degrees, and substantially 45 degrees.

With reference to FIGS. 22A-22E, illustrated are various views of the shroud portion of the light therapy spot applicator shown in FIGS. 20A and 20B.

Figure 23:
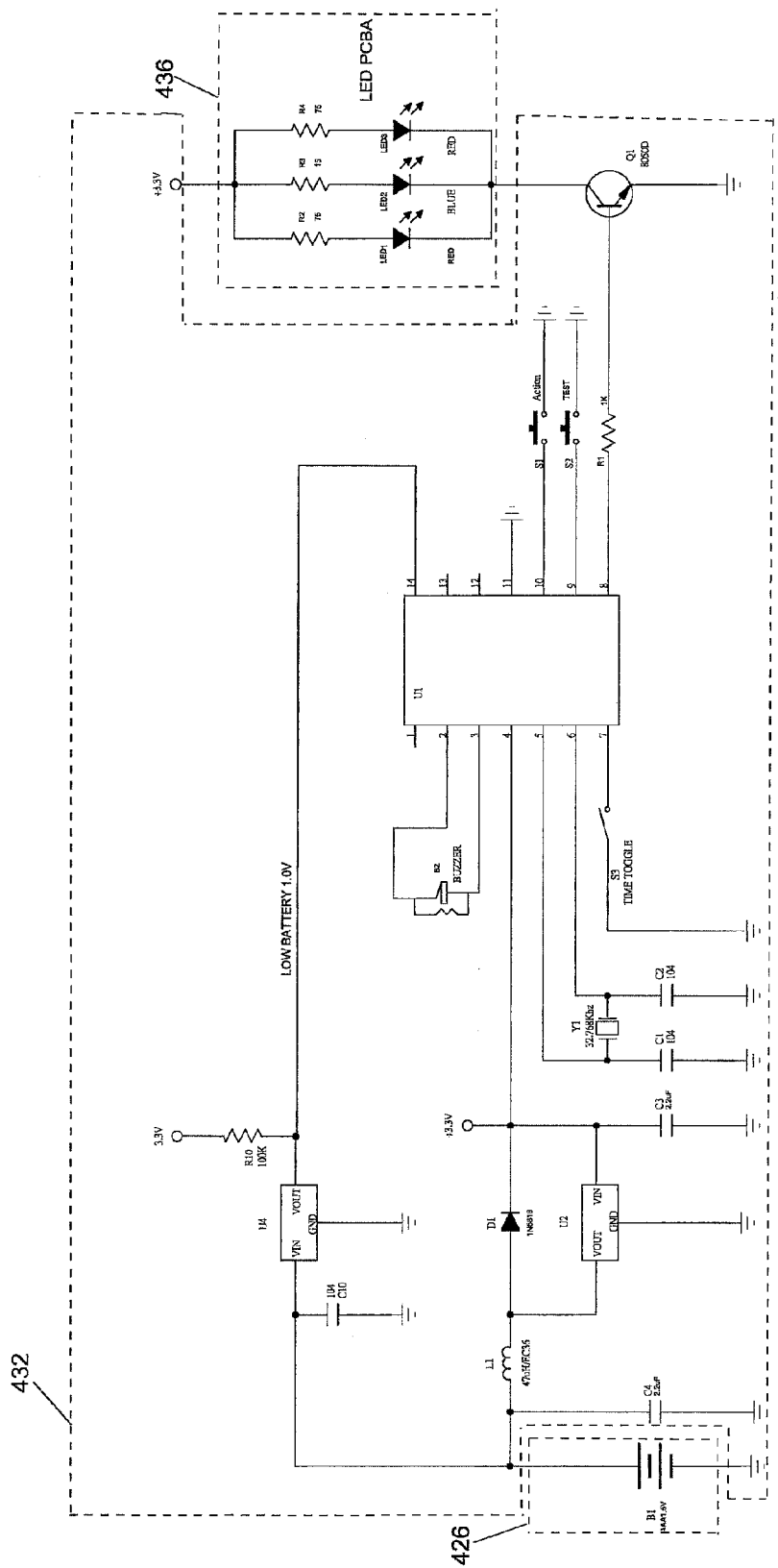
FIG. 23 is an electrical schematic of a light therapy spot applicator according to an exemplary embodiment of this disclosure.

With reference to FIG. 23, shown is an electrical schematic of a light therapy spot applicator according to an exemplary embodiment of this disclosure.

As shown, according to an exemplary embodiment of this disclosure, FIG. 23 includes an arrangement of electronic components operatively associated with the control PCB 432 and LED PCB 436 which provide a functioning light therapy spot application as described herein. Specifically, the electrical components of the device includes battery B1; a low battery voltage circuit including components C10, U4 and R10; a step-up voltage circuit including components C4, L1, D1, C3 and U2; buzzer B2, an oscillator circuit including Y1, C1 and C2; switch circuitry associated with the user controlled button switch 406 including S1 and S2; LED driver circuit Q1, R2, R3 and R4, as well as LEDs LED1, LED2 and LED3. Logic control device U1 provides for the control and operation of the light therapy spot applicator according to instructions provided by an implemented algorithm, as will be further discussed with reference to FIG. 24.

Figure 24:
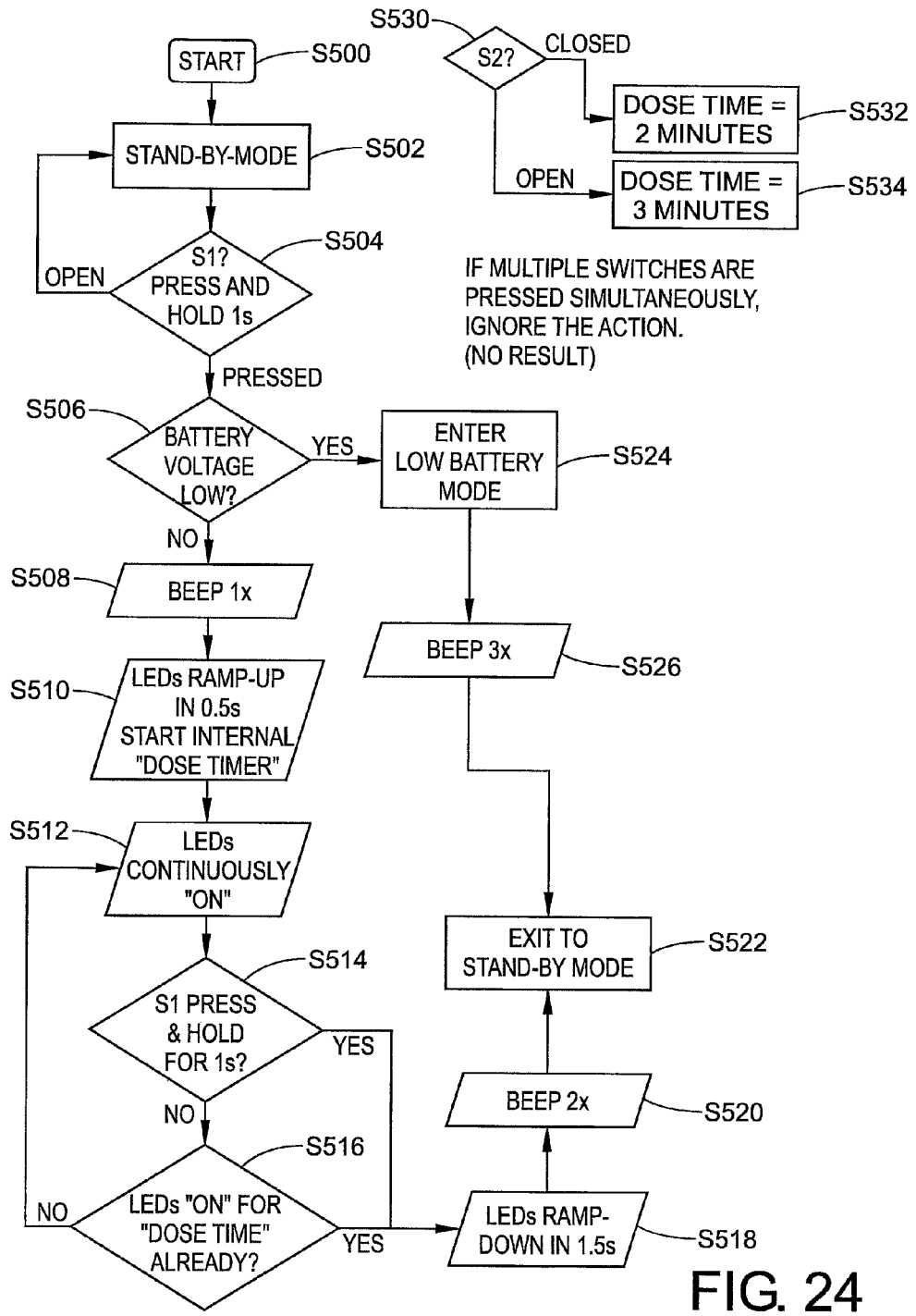
FIG. 24 is an operational logic diagram associated with a light therapy spot applicator according to an exemplary embodiment of this disclosure.

With reference to FIG. 24, shown is an operational logic diagram associated with a light therapy spot applicator according to an exemplary embodiment of this disclosure.

As shown, the control algorithm operates as follows:

At step S500, the control algorithm starts and remains in a Stand-By-Mode until activation of the user controller button switch 406.

Next, at step S502, the control algorithm remains in a Stand-By-Mode until the S1 switch contacts are closed for 1 second at S504, associated with a user depressing control button switch 406.

Next, the control algorithm determines if the battery voltage is low at step S506, if the battery voltage is low, the control algorithm enters a Low Battery Mode at step S524 and activates Buzzer B2 at step S526 to notify the user the battery needs to be replaced/re-charged, and the control algorithm exits to Stand-By-Mode at step S522 until the device is turned off.

If the control algorithm determines battery voltage is not low at step S506, the device activates Buzzer B2 at S508 and beeps once to notify the user the device is beginning a light therapy dosing session.

At step S510, the control algorithm ramps-up the LEDs to the desired dosage power in 0-5 seconds and initializes an internal dosage timer.

At step S512, the control algorithm continuously drives the LEDs at the desired power until the user presses and holds button control switch 406 for 1 second or the control algorithm determines the LEDs have been on for a continuous period of time associated with a predetermined dosage time duration at step S516.

After either steps S514 and S516 determine it is appropriate to end a light therapy dosage session, at step S518 the control algorithm ramps down the power delivered by the LEDs in a predetermined amount of time, e.g., 1.5 seconds.

Next, at step S520 the control algorithm activates Buzzer B2 and provides two beeps to notify the user the light therapy dosing session has ended.

Finally, the control algorithm exits to Stand-By-Mode at step S502.

Some portions of the detailed description herein are presented in terms of algorithms and symbolic representations of operations on data bits performed by conventional computer components, including a central processing unit (CPU), memory storage devices for the CPU, and connected display devices. These algorithmic descriptions and representations are the means used by those skilled in the data processing arts to most effectively convey the substance of their work to others skilled in the art. An algorithm is generally perceived as a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be understood, however, that all of these and similar terms are to be associated with the appropriate physical quantities and are merely convenient labels applied to these quantities. Unless specifically stated otherwise, as apparent from the discussion herein, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The exemplary embodiment also relates to an apparatus for performing the operations discussed herein. This apparatus may be specially constructed for the required purposes, or it may comprise a general-purpose computer selectively activated or reconfigured by a computer program stored in the computer. Such a computer program may be stored in a computer readable storage medium, such as, but is not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, and each coupled to a computer system bus.

The algorithms and displays presented herein are not inherently related to any particular computer or other apparatus. Various general-purpose systems may be used with programs in accordance with the teachings herein, or it may prove convenient to construct more specialized apparatus to perform the methods described herein. The structure for a variety of these systems is apparent from the description above. In addition, the exemplary embodiment is not described with reference to any particular programming language. It will be appreciated that a variety of programming languages may be used to implement the teachings of the exemplary embodiment as described herein.

A machine-readable medium includes any mechanism for storing or transmitting information in a form readable by a machine (e.g., a computer). For instance, a machine-readable medium includes read only memory ("ROM"); random access memory ("RAM"); magnetic disk storage media; optical storage media; flash memory devices; and electrical, optical, acoustical or other form of propagated signals (e.g., carrier waves, infrared signals, digital signals, etc.), just to mention a few examples.

The methods illustrated throughout the specification, may be implemented in a computer program product that may be executed on a computer. The computer program product may comprise a non-transitory computer-readable recording medium on which a control program is recorded, such as a disk, hard drive, or the like. Common forms of non-transitory computer-readable media include, for example, floppy disks, flexible disks, hard disks, magnetic tape, or any other magnetic storage medium, CD-ROM, DVD, or any other optical medium, a RAM, a PROM, an EPROM, a FLASH-EPROM, or other memory chip or cartridge, or any other tangible medium from which a computer can read and use.

Alternatively, the method may be implemented in transitory media, such as a transmittable carrier wave in which the control program is embodied as a data signal using transmission media, such as acoustic or light waves, such as those generated during radio wave and infrared data communications, and the like.

It will be appreciated that variants of the above-disclosed and other features and functions, or alternatives thereof, may be combined into many other different systems or applications. Various presently unforeseen or unanticipated alternatives, modifications, variations or improvements therein may be subsequently made by those skilled in the art which are also intended to be encompassed by the following claims.

What is claimed is:

1. A phototherapy device comprising:
   a tubular body including a longitudinal length extending between a first end of the tubular body and a second end of the tubular body, the tubular body housing a plurality of radiant lamps having a mixed combination of different wavelength radiant energy proximately located near the first end of the tubular body;
   a first end surface located at the first end of the tubular body, the first end surface including a concave surface and a radiant energy communication area recessed from a protruding peripheral surface of the first end surface, the concave surface and radiant energy communication area configured to direct the radiant energy from the plurality of radiant lamps to a user treatment area along an angular offset axis angularly offset 15 degrees to 75 degrees from a longitudinal axis associated with the longitudinal length of the tubular body, wherein the first end surface traps the radiant energy from the plurality of radiant lamps within a confine limited by the concave surface, the recessed radiant energy communication area, the protruding peripheral surface of the first end surface and the user treatment area with the first end surface in contact with an area about the user treatment area; and
   a second end surface located at the second end of the tubular body.

2. The phototherapy device according to claim 1, wherein the protruding peripheral surface is configured to direct the radiant energy from the plurality of radiant lamps at a non-normal incident angle relative to the user treatment area with the protruding peripheral surface in contact with the area about the user treatment area.

3. The phototherapy device according to claim 1, the tubular body further comprising:
   a main circuit board housed within the tubular body;
   one or more batteries; and
   a control button,
      wherein the main circuit board, the one or more batteries and the control button are operatively connected to control the plurality of radiant lamps.

4. The phototherapy device according to claim 1, further comprising:

a fixed cover over the plurality of radiant lamps, the fixed cover transparent to the radiant energy communicated from the plurality of radiant lamps to the user treatment area.

5. The phototherapy device according to claim 1, wherein the concave surface includes one or more apertures for communicating the radiant energy to the user treatment area.

6. The phototherapy device according to claim 1, further comprising:
a controller configured to control a radiant energy dosage time duration.

7. The phototherapy device according to claim 6, wherein the radiant energy dosage time duration is 2 minutes to 3 minutes.

8. The phototherapy device according to claim 1, the tubular body further comprising:
a single battery housed within the tubular body; and
a step-up voltage circuit operatively associated with the single battery and one or more of the plurality of radiant lamps, the step-up voltage circuit configured to step-up a voltage provided by the single battery to drive one or more of the plurality of radiant lamps.

9. A phototherapy device comprising:
a tubular body including a longitudinal length extending between a first end of the tubular body and a second end of the tubular body, the tubular body housing one or more radiant lamps proximately located near the first end of the tubular body, the one or more radiant lamps disposed to communicate radiant energy to a user treatment area;
a first end surface located at the first end of the tubular body, the first end surface including a concave surface and a radiant energy communication area recessed from a protruding peripheral surface of the first end surface, the concave surface and radiant energy communication area configured to direct the radiant energy from the one or more radiant lamps to the user treatment area along an angular offset axis angularly offset 15 degrees to 75 degrees from a longitudinal axis associated with the longitudinal length of the tubular body, wherein the first end surface traps the radiant energy from the plurality of radiant lamps within a confine limited by the concave surface, the recessed radiant energy communication area, the protruding peripheral surface of the first end surface and the user treatment area with the first end surface in contact with an area about the user treatment area; and
a second end surface located at the second end of the tubular body.

10. The phototherapy device according to claim 9, wherein the protruding peripheral is configured to direct the radiant energy from the one or more radiant lamps at a non-normal incident angle relative to the user treatment area with the protruding peripheral surface in contact with the area about the user treatment area.

11. The phototherapy device according to claim 9, the tubular body further comprising:
a main circuit board housed within the tubular body;
one or more batteries; and
a control button,
wherein the main circuit board, the one or more batteries and the control button are operatively connected to control the one or more radiant lamps.

12. The phototherapy device according to claim 9, further comprising:
a fixed cover over the plurality of radiant lamps, the fixed cover transparent to the radiant energy communicated from the one or more radiant lamps to the user treatment area.

13. The phototherapy device according to claim 9, wherein the concave surface includes one or more apertures for communicating the radiant energy to the user treatment area.

14. The phototherapy device according to claim 9, further comprising:
a controller configured to control a radiant energy dosage time duration.

15. The phototherapy device according to claim 14, wherein the radiant energy dosage time duration is 2 minutes to 3 minutes.

16. The phototherapy device according to claim 9, the tubular body further comprising:
a single battery housed within the tubular body; and
a step-up voltage circuit operatively associated with the single battery and one or more of the plurality of radiant lamps, the step-up voltage circuit configured to step-up a voltage provided by the single battery to drive the one or more radiant lamps.

17. A phototherapy device comprising:
a tubular body including a longitudinal length extending between a first end of the tubular body and a second end of the tubular body, the tubular body housing one or more radiant lamps proximately located near the first end of the tubular body, the one or more radiant lamps disposed to communicate radiant energy to a user treatment area;
a first end surface located at the first end of the tubular body, the first end surface including a radiant energy communication area recessed from a protruding peripheral surface of the first end surface, the first end surface and radiant energy communication area directing the radiant energy from the one or more radiant lamps to the user treatment area along an angular offset axis angularly offset 15 degrees to 75 degrees from a longitudinal axis associated with the longitudinal length of the tubular body and the first end surface trapping the radiant energy from the one or more radiant lamps within a confine limited by the first end surface, the recessed radiant energy communication area, the protruding peripheral surface of the first end surface and the user treatment area with the first end surface in contact with an area about the user treatment area; and
a second end surface located at the second end of the tubular body.

18. The phototherapy device according to claim 17, wherein the protruding peripheral surface is configured to direct the radiant energy from the one or more radiant lamps at a non-normal incident angle relative to the user treatment area with the protruding peripheral surface in contact with the area about the user treatment area.

19. The phototherapy device according to claim 17, the tubular body further comprising:
a main circuit board housed within the tubular body;
one or more batteries; and
a control button,
wherein the main circuit board, the one or more batteries and the control button are operatively connected to control the one or more radiant lamps.

20. The phototherapy device according to claim 17, further comprising:

a fixed cover over the one or more radiant lamps, the fixed cover transparent to the radiant energy communicated from the one or more radiant lamps to the user treatment area.

21. The phototherapy device according to claim 17, wherein the first end surface includes one or more apertures for communicating the radiant energy to the user treatment area.

22. The phototherapy device according to claim 17, further comprising:
   a controller configured to control a radiant energy dosage time duration.

23. The phototherapy device according to claim 22, wherein the radiant energy dosage time duration is 2 minutes to 3 minutes.

24. The phototherapy device according to claim 17, the tubular body further comprising:
   a single battery housed within the tubular body; and
   a step-up voltage circuit operatively associated with the single battery and the one or more radiant lamps, the step-up voltage circuit configured to step-up a voltage provided by the single battery to drive the one or more radiant lamps.

\* \* \* \* \*